(12) United States Patent
Hara et al.

(10) Patent No.: US 10,932,747 B2
(45) Date of Patent: Mar. 2, 2021

(54) RADIATION IMAGING SYSTEM

(71) Applicant: Konica Minolta, Inc., Tokyo (JP)

(72) Inventors: Kentaro Hara, Hino (JP); Nobuyuki Miyake, Yokohama (JP); Masahiro Kuwata, Machida (JP); Kohei Isogai, Kawasaki (JP); Koji Kashima, Higashiyamato (JP); Hidetake Tezuka, Tachikawa (JP)

(73) Assignee: KONICA MINOLTA, INC., Tokyo (JP)

( * ) Notice: Subject to any disclaimer, the term of this patent is extended or adjusted under 35 U.S.C. 154(b) by 55 days.

(21) Appl. No.: 16/360,517

(22) Filed: Mar. 21, 2019

(65) Prior Publication Data

US 2019/0290238 A1    Sep. 26, 2019

(30) Foreign Application Priority Data

Mar. 23, 2018   (JP) .............. JP2018-056231

(51) Int. Cl.
*A61B 6/00* (2006.01)

(52) U.S. Cl.
CPC ............ *A61B 6/566* (2013.01); *A61B 6/4233* (2013.01); *A61B 6/4494* (2013.01); *A61B 6/563* (2013.01)

(58) Field of Classification Search
CPC ...... A61B 6/566; A61B 6/4233; A61B 6/4494; A61B 6/563; A61B 6/542
See application file for complete search history.

(56) References Cited

U.S. PATENT DOCUMENTS

| | | | |
|---|---|---|---|
| 7,706,505 B2 | 4/2010 | Tachikawa | |
| 8,704,188 B2 | 4/2014 | Kitano et al. | |
| 2013/0102245 A1* | 4/2013 | Ohguri | A61B 6/548 |
| | | | 455/39 |

FOREIGN PATENT DOCUMENTS

| | | |
|---|---|---|
| JP | 5127492 B2 | 1/2013 |
| JP | 5300832 B2 | 9/2013 |
| JP | 5479560 B2 | 4/2014 |
| JP | 5917580 B2 | 5/2016 |
| JP | 2017029410 A | 2/2017 |

* cited by examiner

*Primary Examiner* — Courtney D Thomas
(74) *Attorney, Agent, or Firm* — Cantor Colburn LLP

(57) ABSTRACT

A synchronization signal transmitter is configured to be capable of storing unique identification information that can identify the synchronization signal transmitter and transmitting the identification information to a radiation irradiation apparatus and a radiation imaging apparatus. The radiation irradiation apparatus or the radiation imaging apparatus includes a hardware processor that determines whether or not the identification information that has been received by the radiation irradiation apparatus and the identification information received by the radiation imaging apparatus are in agreement with each other.

7 Claims, 10 Drawing Sheets

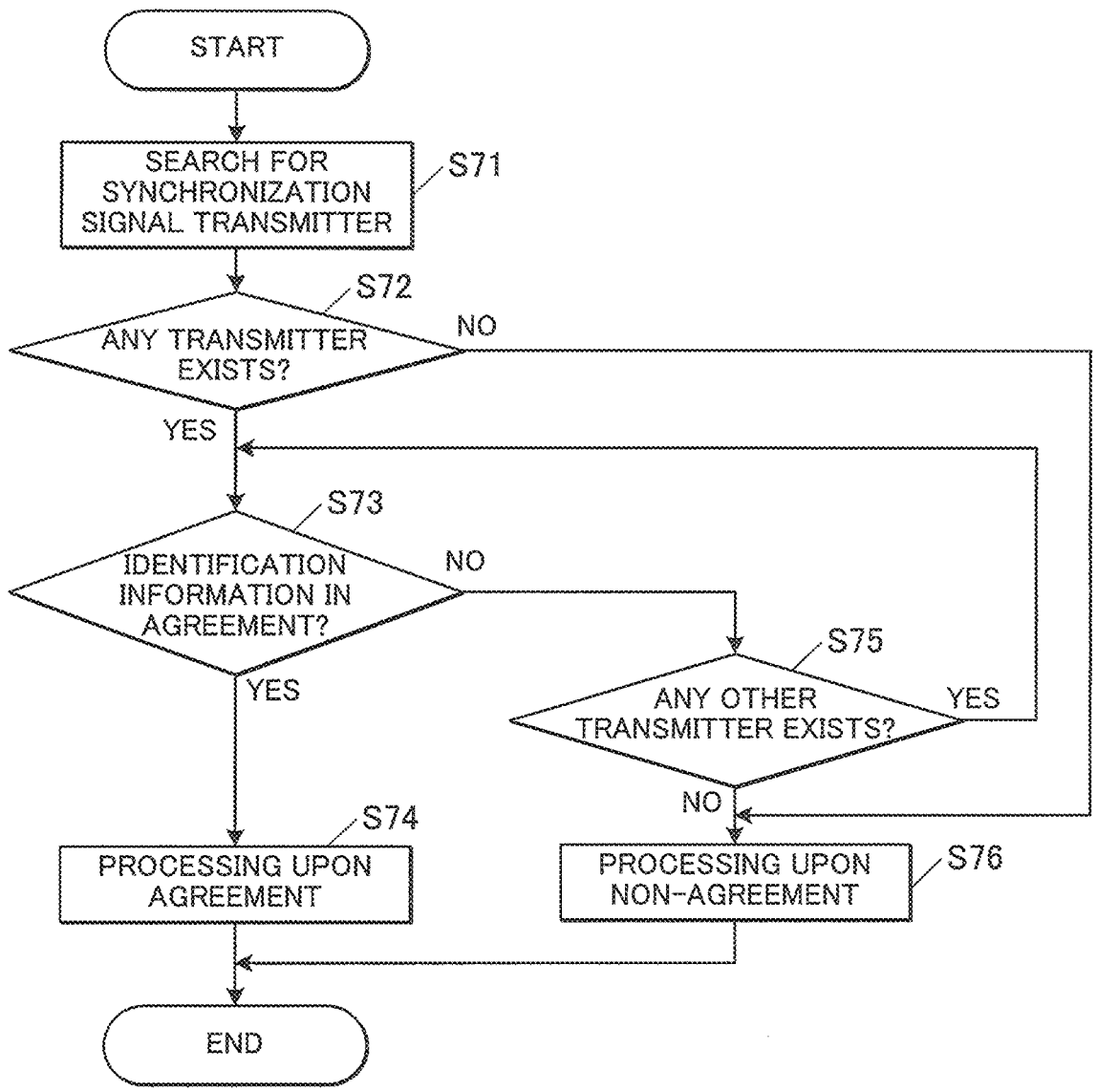

RADIATION IMAGING SYSTEM

CROSS REFERENCE TO RELATED APPLICATION

The present application claims priority under 35 U.S.C. § 119 to Japanese Application No. 2018-056231, filed Mar. 23, 2018, the entire content of which is incorporated herein by reference.

BACKGROUND

Technical Field

The present invention relates to a radiation imaging system.

Description of the Related Art

Various techniques have been traditionally proposed for a radiation imaging system that synchronizes individual operations between a radiation irradiation apparatus that generates radiation and a radiation imaging apparatus that generates image data of a radiographic image in accordance with the received radiation by using a synchronization signal transmitted by a synchronization signal generator.

Some of such techniques may be mentioned here, amongst others, for example, a technique that switches between pieces of wireless connection information in accordance with an instruction by wired connection (see Japanese Patent No. 5300832 and U.S. Pat. No. 8,704,188), a technique that determines whether an X-ray imaging apparatus act as a master or slave wireless device so as to configure an interference-free wireless network (see Japanese Patent Application Laid-Open No. 2017-029410), and a technique that adjusts X-ray irradiation timing and accumulation timing of an FPD panel by ensuring synchronization between a timer of the X-ray generation device and that of the FPD panel (see Japanese Patent Nos. 5127492, 5479560, 5917580; and U.S. Pat. No. 7,706,505).

However, the above-described techniques are all directed to identification of wireless networks. Meanwhile, a wireless network configured in accordance with IEEE 802.11, which is a communication standard that has been recently typically used, allows creation of the same network by multiple devices. In other words, a situation may occur in which the individual devices constituting the radiation imaging system receive synchronization signals from different access points. Since the transmission timings of the synchronization signals of the individual access points does not always completely coincide with each other, a signal transmitted by an access point is of low reliability as a synchronization signal, which is a drawback found in these techniques.

Also, the above-mentioned techniques cannot be used if the individual devices do not establish a radio link to the access point.

SUMMARY

A problem of the present invention is to make it possible to determine whether or not the radiation irradiation apparatus and the radiation imaging apparatus are allowed to receive the synchronization signal from the same synchronization signal transmitter even multiple synchronization signal transmitters exist in a radiation imaging system that includes a radiation irradiation apparatus which generates radiation, a radiation imaging apparatus which generates image data of a radiographic image in accordance with a received radiation, and a synchronization signal transmitter which transmits a synchronization signal to these devices.

To achieve at least one of the abovementioned objects, according to a first aspect of the present invention, radiation imaging system reflecting one aspect of the present invention comprises a radiation irradiation apparatus that generates radiation;

a radiation imaging apparatus that generates image data of a radiographic image in accordance with the radiation emitted; and a synchronization signal transmitter connected to the radiation irradiation apparatus or incorporated in the radiation irradiation apparatus.

The synchronization signal transmitter transmits a synchronization signal to the radiation imaging apparatus. The synchronization signal is used to synchronize operations between the radiation imaging apparatus and the radiation irradiation apparatus.

The synchronization signal transmitter stores unique identification information used to identify the synchronization signal transmitter and transmits the identification information to the radiation irradiation apparatus and the radiation imaging apparatus, respectively.

The radiation irradiation apparatus or the radiation imaging apparatus includes a hardware processor that determines whether or not the identification information received by the radiation irradiation apparatus and the identification information received by the radiation imaging apparatus are in agreement with each other.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 18 is a flowchart illustrating the processing performed by the radiation imaging system according to Example 2-3.

DETAILED DESCRIPTION OF EMBODIMENTS

Hereinafter, one or more embodiment of the present invention will be described with reference to the drawings. However, the scope of the invention is not limited to the disclosed embodiments.

First Embodiment

The first embodiment of the present invention will be described hereinbelow.
(Radiation Imaging System)

Figure 1:
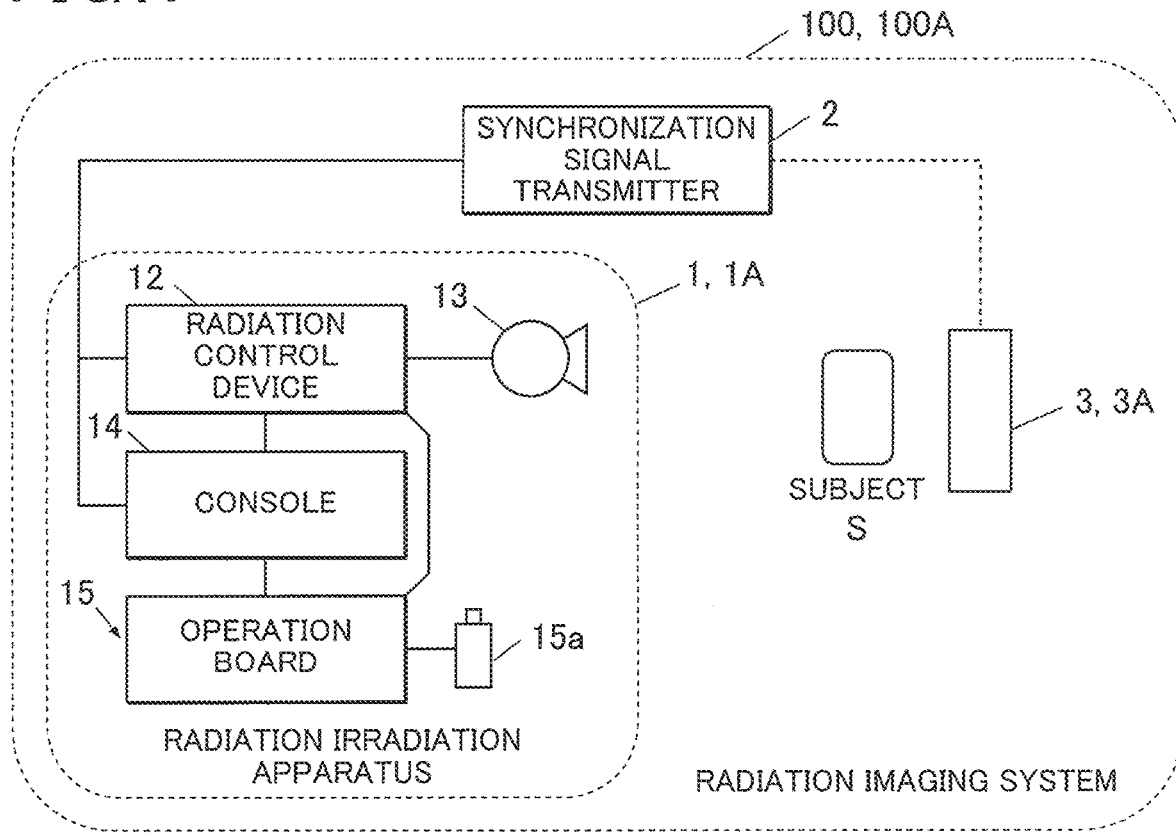
FIG. 1 is a block diagram illustrating a schematic configuration of a radiation imaging system according to first to third embodiments of the present invention.

The outline of the features of a radiation imaging system (hereinafter referred to as "imaging system 100") according to this embodiment will be first described. FIG. 1 is a block diagram that illustrates the schematic configuration of the imaging system 100.

As illustrated in FIG. 1, the imaging system 100 according to this embodiment includes a radiation irradiation apparatus (hereinafter referred to as "irradiation apparatus 1"), a synchronization signal transmitter 2 and one or more radiation imaging apparatuses (hereinafter referred to as "imaging apparatus 3").

Also, the imaging system 100 is capable of performing communications with a radiology information system (RIS), a picture archiving and communication system (PACS), etc.

The irradiation apparatus 1 generates radiation (X-ray, etc.) and emits the generated radiation toward a subject S and an imaging apparatus 3 arranged behind the subject S. The irradiation apparatus 1 includes a housing 11, a radiation control device 12, a radiation source 13, a console 14, an operation board 15, and the like.

Communications can be carried out by wired connection between the radiation control device 12 and the radiation source 13, between the radiation control device 12 and the console 14, between the console 14 and the operation board 15, and between the radiation control device 12 and the operation board 15.

The radiation control device 12 is configured to be capable of applying voltage in accordance with a preset radiation irradiation condition (tube voltage and tube current, irradiation time (a value in milliampere-seconds (mAs)), etc.) to the radiation source 13 in response to an exposure switch 15a having been operated.

It should be noted that details of the radiation control device 12 will be described later.

The radiation source 13 may include, for example, a not-shown rotating anode, a filament, etc.

In addition, when voltage is applied from the radiation controller 12 to the filament, the filament emits an electron beam in accordance with the applied voltage toward the rotating anode and the rotating anode then generates a radiation the dose of which corresponds to the intensity of the electron beam. In other words, the radiation source 13 is configured to emit radiation continuously when voltage is continuously applied from the radiation control device 12 and emit pulsed radiation when a pulsed voltage is applied therefrom.

The console 14 may be configured by a personal computer, a mobile terminal, or a dedicated device and is connected to the radiation control device 12 by wired connection enabling communications therebetween.

Also, the console 14 is capable of receiving image data of the radiographic image from the imaging apparatus 3 and transmitting the image data to an external entity (a picture archiving and communication system (PACS), etc.).

In addition, the console 14 is capable of performing various image processing processes on the received image data as required.

Also, the console 14 has a not-shown display device and is capable of displaying the radiographic image based on the image data.

In addition, the console 14 is capable of specifying radiation irradiation conditions (e.g., tube voltage and tube current, irradiation time, etc.) on the basis of an imaging order from an external device (a radiology information system (RIS), etc.) and an operation by a user.

Also, the console 14 is capable of specifying photographing modes.

This embodiment envisages two photographing modes, i.e., a still image photographing mode and a kymography mode, either of which is selected by the console 14.

The still image photographing mode is a photographing mode in which one single depression of an exposure switch 15a triggers only one round of irradiation of a radiation having a duration specified according to the irradiation condition so as to generate one single radiographic image.

The kymography mode is another photographing mode in which one single depression of the exposure switch 15a triggers one or more rounds of irradiation of pulsed radiation having the duration specified according to the irradiation condition so as to generate one or more radiographic images.

Also, the console 14 is capable of specifying a frame rate when the kymography has been specified as the photographing mode. The frame rate may be given as any appropriate value entered by a user or may be selected from several candidates (e.g., 15 frames per second (hereinafter referred to as fps), 7.5 fps, 30 fps, etc.).

The operation board 15 has the exposure switch 15a of two-stage configuration.

The exposure switch 15a is connected to the body of the operation board 15 by wired connection.

In addition, the exposure switch 15a is configured to trigger transmission of an imaging start signal to the radiation control device 12 and the imaging apparatus 3 in response to the exposure switch 15a having been operated.

The synchronization signal transmitter 2 of this embodiment is connected to the irradiation apparatus 1 by wired connection enabling communications therewith and is connected to the imaging apparatus 3 by wireless connection enabling communications therewith.

Also, the synchronization signal transmitter 2 of this embodiment is configured to function as an access point for wireless communications and relay the communications between the irradiation apparatus 1 and the imaging apparatus 3.

It should be noted that while FIG. 1 illustrates an example where the synchronization signal transmitter 2 is provided as an independent device that is different than the irradiation apparatus 1 and is connected to the irradiation apparatus 1 by wired connection, the synchronization signal transmitter 2 may alternatively be incorporated in the irradiation apparatus 1.

Details of the synchronization signal transmitter 2 will be described later.

The imaging apparatus 3 generates an image data of the radiographic image in accordance with the radiation emitted from the irradiation apparatus 1.

Also, the imaging apparatus 3 is capable of performing communications with the irradiation apparatus 1 via the synchronization signal transmitter 2. Specifically, the imaging apparatus 3 is capable of receiving various signals from the irradiation apparatus 1 and transmitting the generated image data to the irradiation apparatus 1.

It should be noted that details of the imaging apparatus 3 will be described later.

The imaging system 100 according to this embodiment having the above-described features is capable of performing imaging on the subject S by irradiating the subject S arranged in front of the imaging apparatus 3 with the radiation emitted from the irradiation apparatus 1.

In the console 14, one single still image is obtained when the photographing mode is set to the still image photographing mode and the imaging is performed in this mode, and a series of images are obtained when the photographing mode is set to the kymography mode and the imaging is performed in this mode.

The series of images obtained by the kymography is hereinafter referred to as "moving image" and the individual images constituting the moving image are hereinafter referred to as "frame images."

Also, the imaging system 100 according to this embodiment having the above-described features may be installed, for example, in an imaging room of a hospital for actual use and may also be used as a movable system by configuring the irradiation apparatus 1 as a wheeled visiting car. When it is movable, it is made possible to obtain a radiographic image of the subject S at the place of the subject S who may not be able to move.

(Radiation Control Device)

Figure 2:
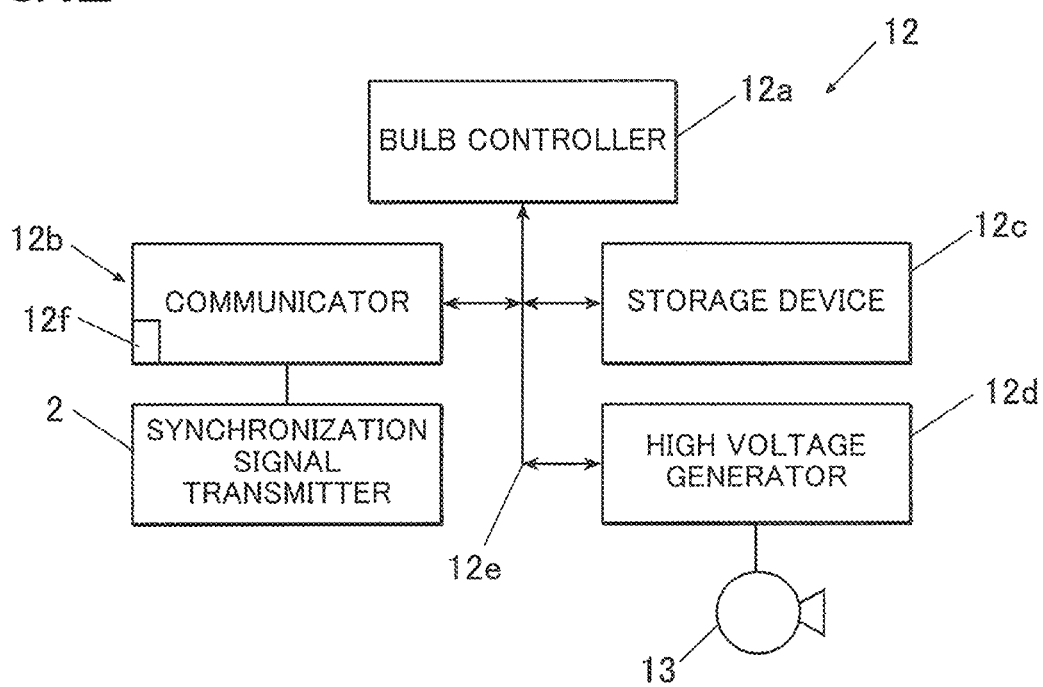
FIG. 2 is a block diagram illustrating a specific configuration of a radiation control device provided in the radiation imaging system of FIG. 1.

Next, radiation control device 12 provided in the irradiation apparatus 1 of the above-described imaging system 100 will be described in detail below. FIG. 2 is a block diagram illustrating the specific configuration of the radiation control device 12.

As illustrated in FIG. 2, the radiation control device 12 of this embodiment includes a bulb controller 12a, a communicator 12b, a storage device 12c, a high voltage generator 12d, and a bus 12e interconnecting the aforementioned components.

The bulb controller 12a is configured to comprehensively control the operations of the individual components of the radiation control device 12 by means of a CPU, a RAM device, etc. Specifically, the bulb controller 12a reads various processing programs stored in the storage device 12c in response to various events as a trigger such as the power supply being switched on, a predetermined control signal being received from an external device, a radiation being received from the irradiation apparatus 1, and the like; deploys the various processing programs onto the RAM device; and performs various processes in accordance with the programs.

The communicator 12b includes a wired communication interface and is capable of performing transmission and reception of data with an external device connected thereto via a communication network such as a local area network (LAN), a wide area network (WAN), the Internet, etc.

Also, the communicator 12b includes a connector 12f for performing wired communications with the synchronization signal transmitter 2 (for insertion of a cable).

The storage device 12c is configured by a hard disk drive (HDD), a semiconductor memory device, etc. and stores various processing programs including a program for performing various processes associated with image processing as well as parameters, files, etc. necessary for execution of these programs.

The high voltage generator 12d is configured to apply a voltage in accordance with a preset irradiation condition of the radiation to the radiation source 13 in response to the control signal having been received from the bulb controller 12a.

The bulb controller 12a of the radiation control device 12 having the above-described configuration is configured to specify various imaging conditions (conditions related to the subject S such as the section to be imaged, physical constitution and conditions related to irradiation of the radiation such as a tube voltage and a tube current, irradiation time, current-time product, etc.) on the basis of the control signal from the console 14 or the operation board 15.

Also, the bulb controller 12a is configured to cause the high voltage generator 12d to start application of the voltage (irradiation of the radiation) in response to the imaging start signal having been received from the exposure switch 15a.

(Synchronization Signal Transmitter 2)

Figure 3:
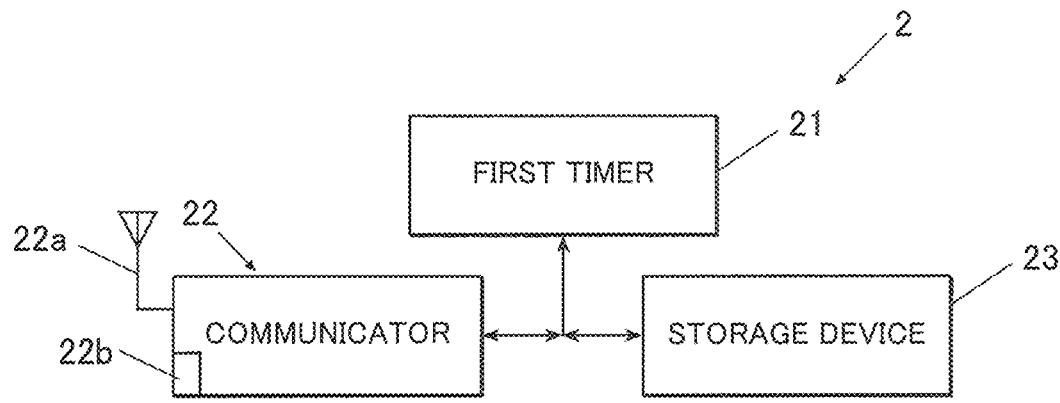
FIG. 3 is a block diagram illustrating a specific configuration of a synchronization signal transmitter provided in the radiation imaging system of FIG. 1.

Next, details of the synchronization signal transmitter 2 provided in the above-described imaging system 100 will be described below. FIG. 3 is a block diagram that illustrates the specific configuration of the synchronization signal transmitter 2.

As illustrated in FIG. 3, the synchronization signal transmitter 2 of this embodiment may include a first timer 21, a communicator 22, a storage device 23, etc.

The first timer 21 is configured to perform counting (timing) in conjunction with the irradiation apparatus 1 in response to the power source having been turned on, a predetermined control signal having been received from an external entity by the communicator 22, or any other event serving as a trigger. Specifically, the first timer 21 is configured to perform the counting in conjunction with a not-shown oscillator incorporated in the count radiation control device 12.

The communicator 22 includes a wired communication interface and a wireless communication interface and is capable of performing transmission and reception of data with an external device connected thereto via a communication network such as a local area network (LAN), a wide area network (WAN), the Internet, etc.

Also, the communicator 22 includes a connector 21b for performing wired communications with the radiation control device 12 (for insertion of a cable) and an antenna 21a for performing transmission and reception of radio waves with the imaging apparatus 3.

The storage device 23 stores unique identification information that can uniquely identify the synchronization signal transmitter 2. As the identification information, for example, a BSSID (the identifier, a MAC address of the synchronization signal transmitter 2), etc. of the synchronization signal transmitter 2 may be mentioned.

It should be noted that it is also possible to use a unique ID which may be given in advance to the synchronization signal transmitter 2. The unique ID may be notified using a radio wave (a beacon, etc. transmitted by the synchronization signal transmitter 2) or by communication, or may be defined by preliminary setting.

Also, if the ESSID and the access key of the synchronization signal transmitter 2 connected to the irradiation apparatus 1 are unique, then the combination of the ESSID and the access key of the synchronization signal transmitter 2 can be used as the identification information.

Whether or not the ESSID and the access key are unique can be determined by scanning of radio waves around the system to ascertain the presence of the synchronization signal transmitter 2.

Use of the combination of an ESSID and an access key will facilitate the necessary procedure because the procedure for confirmation of the identification information can be performed in the course of the wireless connection.

It should be noted that the certainty of uniqueness may be raised in advance, for example, by identifying the wireless channel in advance.

The synchronization signal transmitter 2 having the above-described features is configured to wirelessly transmit a beacon at predetermined intervals (Td). The beacon includes the count value of the first timer 21 at the time of the transmission of the same beacon.

Also, the synchronization signal transmitter 2 is capable of transmitting the identification information to the irradiation apparatus 1 and the imaging apparatus 3. The identification information may be included in the beacon and transmitted or may be transmitted independently of the beacon.

(Configuration of the Radiographic Image Imaging Apparatus)

Figure 4:
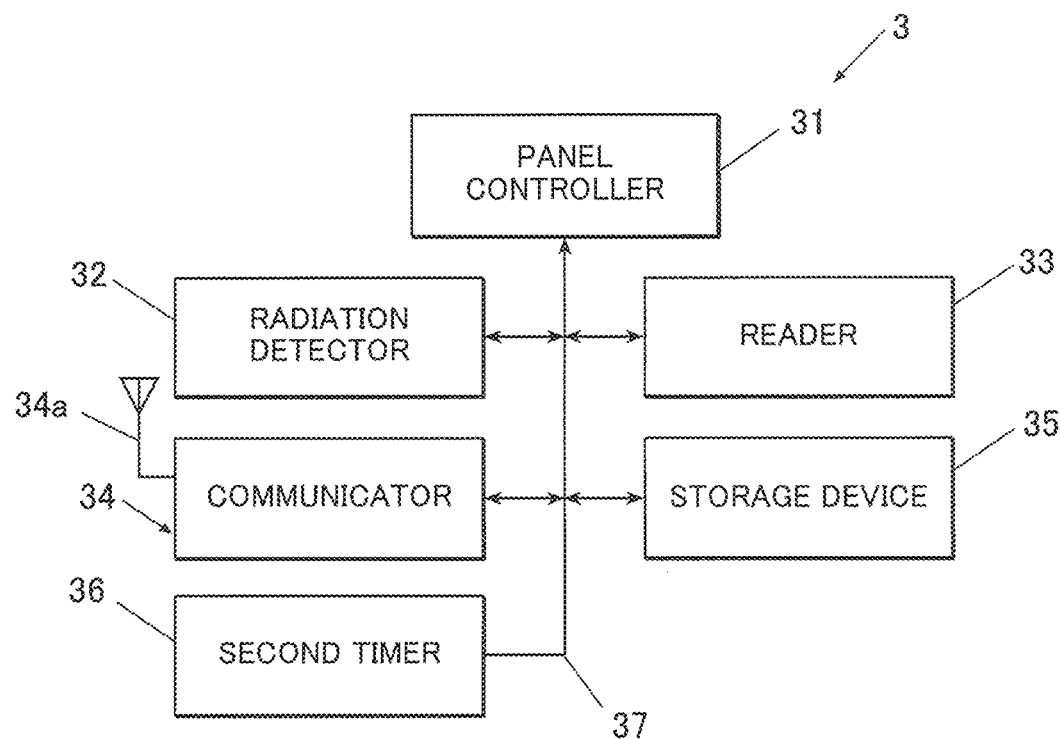
FIG. 4 is a block diagram illustrating a specific configuration of a radiation imaging apparatus provided in the radiation imaging system of FIG. 1.

Next, details of the imaging apparatus 3 constituting the above-described radiation imaging system 100 will be described below. FIG. 4 is a block diagram that illustrates the configuration of the imaging apparatus 3.

As illustrated in FIG. 4, the imaging apparatus 3 includes a panel controller 31, a radiation detector 32, a reader 33, a communicator 34, a storage device 35, a second timer 36, etc. and the individual components 31 to 36 are interconnected via a bus 37. Also, electrical power is supplied from a not-shown built-in battery to the individual components 31 to 36.

The panel controller 31 is configured to comprehensively control the operations of the individual components of the imaging apparatus 3 by means of a CPU, a RAM device, etc. Specifically, the panel controller 31 reads the various processing programs stored in the storage device 35 in response to various events as a trigger such as the power supply being switched on, a predetermined control signal being received from the irradiation apparatus 1 or the console, a radiation being received from the irradiation apparatus 1, and the like; deploys the various processing programs onto the RAM device; and performs various processes in accordance with the programs.

Any traditionally known radiation detector may be used as the radiation detector 32 as long as it has a substrate on which a plurality of pixels are two-dimensionally arranged having a radiation detection element directly or indirectly generating electric charge by an amount corresponding to the dose of the radiation and having a switch element provided between the individual radiation detection elements and the wires and configured to switch between an enabled state where energization between the radiation detection element and the wire is enabled and a disabled state where the energization is disabled.

In other words, the imaging apparatus 3 may have a typical indirect configuration that includes a scintillator and detects the light emitted by the scintillator receiving radiation or may have a typical direct configuration that detects the radiation directly without using a scintillator, etc.

Any traditionally known reader may be used as the reader 33 as long as it is configured to be capable of reading the amount of electric charge accumulated in each of the multiple radiation detection elements as a signal value.

The communicator 34 includes a wireless communication interface and performs transmission and reception of data with an external device connected thereto via a communication network such as a local area network (LAN), a wide area network (WAN), the Internet, etc.

Also, the communicator 34 includes an antenna 34a for performing transmission and reception of radio waves with the synchronization signal transmitter 2.

The storage device 35 is configured by a hard disk drive (HDD), a semiconductor memory device, etc. and stores various processing programs including a program for performing various processes associated with image processing as well as parameters, files, etc. necessary for execution of these programs.

The second timer 36 is configured to perform counting (timing) in response to various events as a trigger such as the power supply being turned on, a predetermined control signal being received from an external entity by the communicator 22.

The panel controller 31 of the imaging apparatus 3 having the above-described features performs the following operations in accordance with the processing programs stored in the storage device 35.

For example, the panel controller 31 has the function of selectably enabling and disabling the switch element of the radiation detector 32.

Also, the panel controller 31 has the function of generating image data of the radiographic image on the basis of the signal value read by the reader 33.

(Imaging Operation by the Radiation Imaging System)

Figure 5:
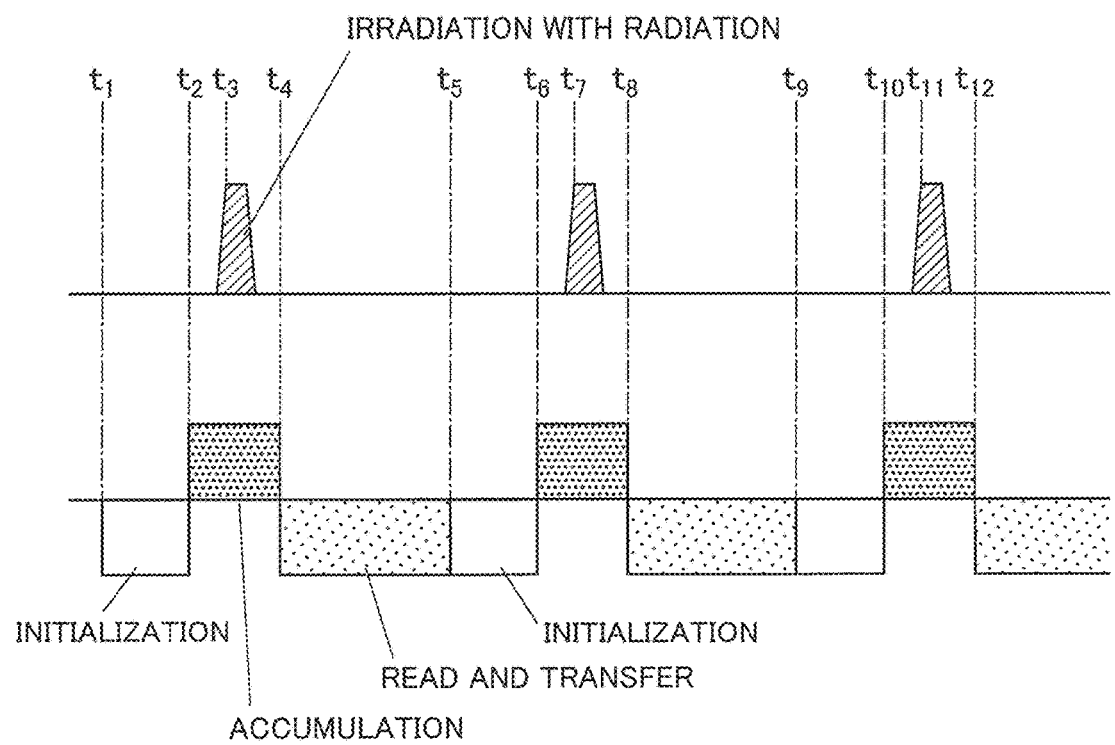
FIG. 5 is a timing chart illustrating the basic operation of the radiation imaging system of FIG. 1.

Next, the basic imaging operation performed by the above-described imaging system 100 will be described below. FIG. 5 is a timing chart that illustrates the operation of the imaging system 100.

First, when an operation is performed which serves as the trigger to start timing by the irradiation-side timekeeper 125 of the control device 12 and the imaging-side timekeeper 37 of the imaging apparatus 3 (e.g., the power supplies of the respective devices of the imaging system 100 are turned on), then the first timer 21 and the second timer 36 individually start the timing.

At this point, the point in time at which the timing by the first timer 21 is started differs from the point in time at which the timing by the second timer 36 is started. Meanwhile, the count value of one of these timers or a count value of a timer operating in conjunction with this timer is used to adjust the count value of the other of these timers so that the one corresponds to the other.

Subsequently, when the count value of the second timer 36 reaches a first predetermined value (t1) (a predetermined first period of time (t1) has elapsed since the timing was started), then the imaging apparatus 3 makes a transition to the "initialization state." The imaging apparatus 3 that has entered the initialization state places the respective switch elements in the enabled state and thereby performs the initialization to release the dark charges accumulated in each pixel.

Subsequently, when the count value of the second timer 36 reaches a second predetermined value (t2) which is greater than the first predetermined value (a second predetermined period of time (t2) has elapsed since the timing was started), then the imaging apparatus 3 makes a transition from the initialization state to the "accumulation state." The imaging apparatus 3 that has entered the accumulation state establishes a disabled state in relation to the respective scanning lines 32b, as a result of which the electric charges generated by the radiation detection elements are now allowed to be accumulated in the pixels. The accumulation state is maintained until the count value of the second timer 36 reaches a fourth predetermined value (t4) which is greater than the second predetermined value (until the fourth predetermined period of time elapses after the start of the timing).

Also, when the count value of the first timer 21 reaches a third predetermined value (t3) greater than the second predetermined value and smaller than the fourth predetermined value (when a third predetermined period of time has elapsed since the timing was started), then the irradiation apparatus 1 emits radiation toward the subject S and the imaging apparatus 3 behind the subject S. In other words, the irradiation apparatus 1 emits the radiation while the imaging apparatus 3 is placed in the accumulation state (t2 to t3).

In addition, imaging apparatus 3 having received the radiation generates electric charges at the respective radiation detection elements 32d of the radiation detector 32 and accumulates them in the respective pixels.

Also, when the count value of the second timer 36 reaches the fourth predetermined value (t4) which is greater than the third predetermined value (when the fourth predetermined period of time (t4) has elapsed since the timing was started), then the imaging apparatus 3 makes a transition from the accumulation state to the "read and transfer state." The imaging apparatus 3 that has entered the read and transfer state places the respective switch elements in the enabled state in the same process flow as in the initialization and releases the electric charges accumulated in the respective pixels. In addition, the reader 33 reads the image data based on the electric charges that have flowed in.

If the photographing mode is set to the kymography mode, the irradiation apparatus 1 and the imaging apparatus 3 repeat the above-described series of operations for the number of rounds corresponding to the number of frame images to be imaged on the basis of the count values of the first timer 21 and the second timer 36.

It should be noted that the accumulated electric charges may be released at the time of reading of the electric charges to perform the initialization operation depending on the configuration of the radiation detection element of the imaging apparatus 3.

(Synchronization Control)

Figure 6:
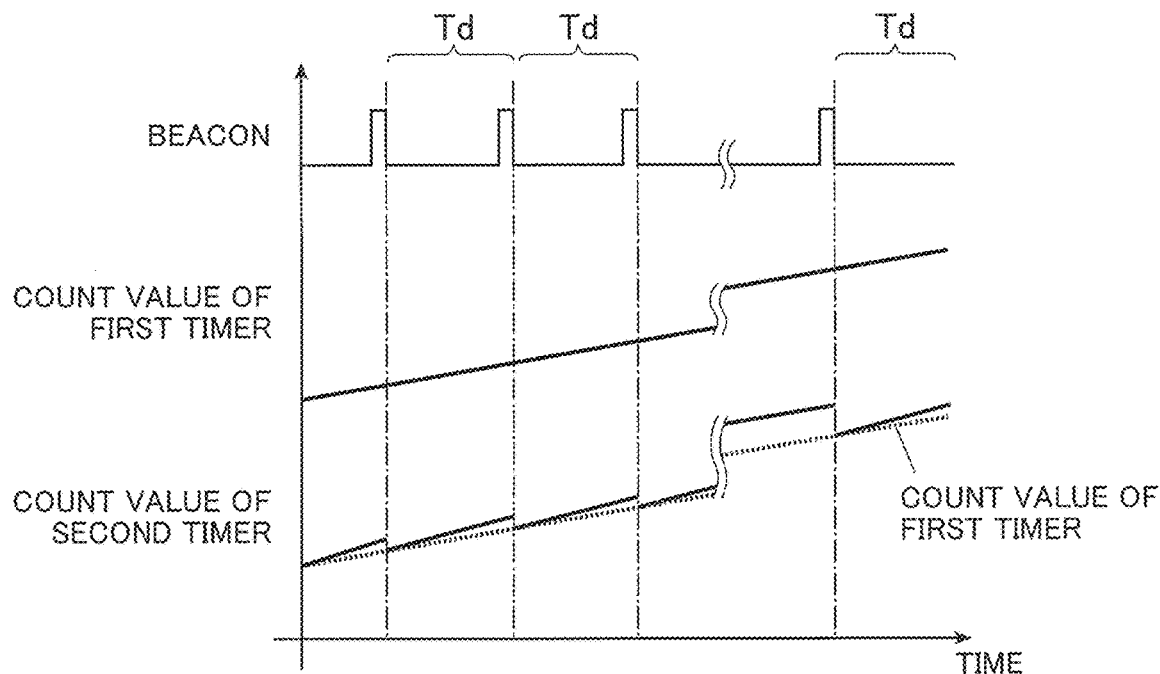
FIG. 6 is a timing chart illustrating an example of synchronization control of the radiation imaging system of FIG. 1.

Next, details of the synchronization control performed by the imaging system 100 according to this embodiment will be described below. FIG. 6 is a timing chart that illustrates the operation of the imaging system 100.

For example, in some cases, there may be a slight difference between the speed of counting of the first timer 21 operating in conjunction with the irradiation apparatus 1 (or provided in the synchronization signal transmitter 2) and the speed of counting of the second timer 36 provided in the imaging apparatus 3 due to influences of error in the frequencies of the oscillators provided in the radiation control device 12 and the imaging apparatus 3 or any other relevant factors. In such a case, if imaging is performed for a relatively long period of time as in the case of kymography, the gap between the count value of the first timer 21 and the count value of the second timer 36 gradually increases, causing a gap between the operation timing of the irradiation apparatus 1 and the operation timing of the imaging apparatus 3.

In view of this, the imaging system 100 according to this embodiment is configured to correct the gap between the operation timing of the irradiation apparatus 1 and the operation timing of the imaging apparatus 3 in order to make it possible to perform the operation illustrated in FIG. 6 even in such a case, i.e., to make it possible to emit radiation by the irradiation apparatus 1 when the imaging apparatus 3 is in the "accumulation state."

As described above, the irradiation apparatus 1 and the synchronization signal transmitter 2 are interconnected by wired connection. As a result, a delay due to intervention of another device can be prevented, for example, by using a dedicated line that is less likely to cause a temporal delay and/or using the time synchronization feature in accordance with IEEE1588 wired communications so as to bring the irradiation apparatus 1 and the synchronization signal transmitter 2 into synchronization with each other, and thus the accuracy of the time synchronization can be enhanced.

Also, it is made possible to reduce the risk that the synchronization cannot be realized because of a communication failure occurring on a communication channel and caused by intervention of another device which causes the gap in the points in time.

Use of a synchronization correction signal is one of the schemes for correcting the gap between the operation timings.

For example, if the communications between the synchronization signal transmitter 2 and the imaging apparatus 3 are performed as wireless communications compliant with the IEEE 802.11 communication standard, the time synchronization function (TSF) of this communication standard can be used.

The "TSF" function realizes adjustment of time between an access point and a device when wireless communications are to be performed between devices. Specifically, an access point is equipped with a timekeeper (TSF timer) that counts up time periodically (every 1 μs) by free run and the count value is carried by a beacon transmitted periodically (every 100 ms according to the standard) to be transmitted to the terminal together with the beacon. Meanwhile, the terminal is also equipped with a timekeeper that counts up time periodically (every 1 μs) and the count value of its own timing device is updated upon reception of a beacon into the count value included in the beacon and thus the counting up is continued. By virtue of this, the count value of either of these timekeepers is periodically corrected, which makes it possible to bring the devices into synchronization with each other.

When the IEEE 802.11-based wireless communications are to be performed by the radiation imaging system according to this embodiment, the synchronization signal transmitter 2 will act as the above-described access point.

In other words, the communicator 22 of the synchronization signal transmitter 2 repeats the transmission of the beacon to the imaging apparatus 3 at predetermined intervals.

In addition, when a beacon is to be transmitted, the count value of the first timer 21 at this time will be included in the beacon and transmitted to the imaging apparatus 3.

Also, when the IEEE 802.11-based wireless communications are to be performed by the radiation imaging system according to this embodiment, the imaging apparatus 3 will act as the above-described terminal.

In other words, the count value of the first timer 21 included in the beacon will be acquired every time the panel controller 31 of the imaging apparatus 3 receives the beacon.

In addition, the panel controller 31 of the imaging apparatus 3 adjusts the count value of the second timer 36 provided in the device itself so as to correspond to the acquired count value of the first timer.

(Determination of Whether or not the Synchronization Signal is Successfully Received from the Same Synchronization Signal Transmitter 2)

Figure 7:
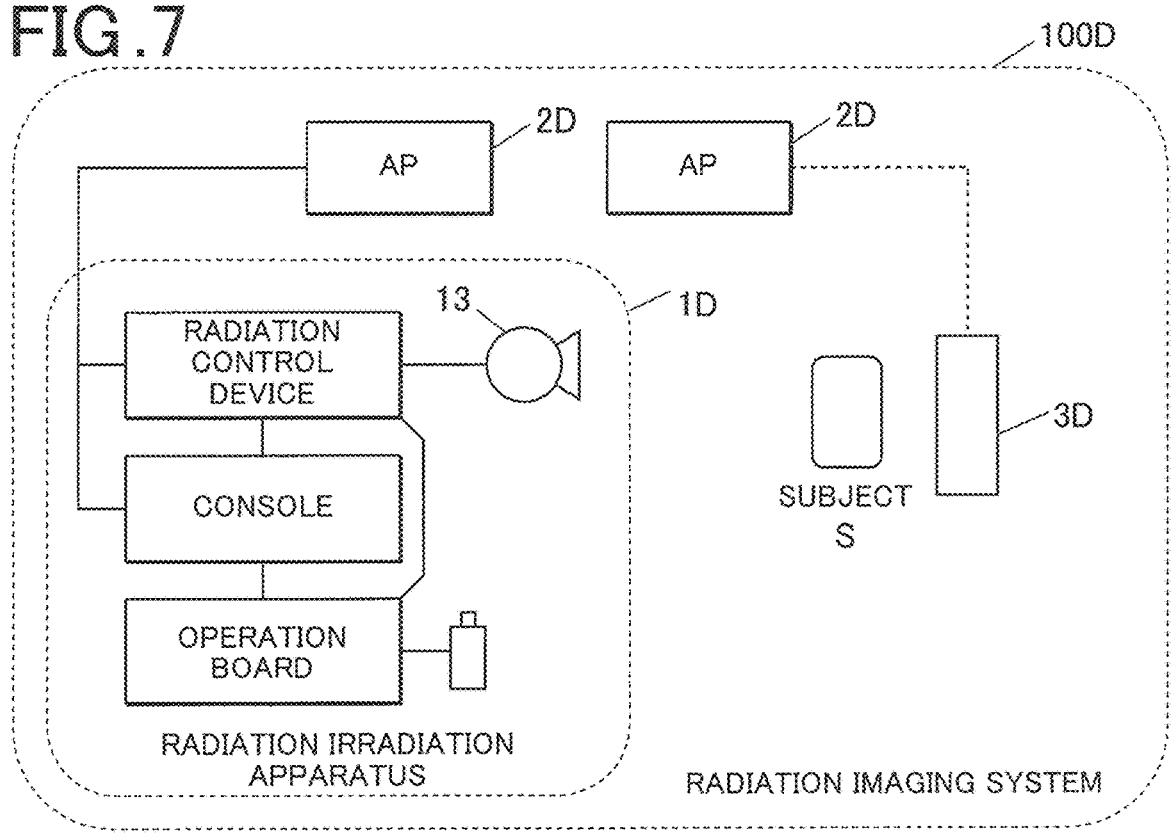
FIG. 7 is a block diagram illustrating a problem that may occur in a conventional radiation imaging system.

In the meantime, when TSF which is available in the above-described IEEE 802.11 communication standard is to be used, the count value of the first timer is unique to each synchronization signal transmitter 2, so that, in order to bring the radiation control device 12 and the radiation imaging apparatus into synchronization with each other correctly, it is necessary that they acquire the count value from the beacon transmitted from the same synchronization signal transmitter 2. In a typical IEEE 802.11-based network, an ESSID is used as the identifier of the synchronization signal transmitter 2, a password is used to establish a wireless link, and thereby the synchronization signal transmitter 2 is identified. Meanwhile, for example, in the conventional radiation imaging system 100D illustrated in FIG. 7, the radiation irradiation apparatus 1D and the radiation imaging apparatus 3D may respectively establish a radio link to different access points residing in the vicinity thereof and having the same setting. Also, if the radio link is not established, it is not possible to identify the synchronization signal transmitter 2, which are the examples of the above-mentioned new problems.

In view of this, in the imaging system 100 according to this embodiment, the irradiation apparatus 1 and the imaging apparatus 3 can uniquely identify the same synchronization signal transmitter 2 in the following manner.

Specifically, the panel controller 31 of the imaging apparatus 3 has the function of receiving identification information from the synchronization signal transmitter 2 near the system via the communicator 34 and transferring it to the irradiation apparatus 1.

At this point, the imaging apparatus 3 may receive the identification information from the synchronization signal transmitter 2 connected thereto or may receive it from an unconnected access point residing near the imaging apparatus 3.

By this configuration, an unconnected access point can be used as the synchronization signal transmitter 2. Also, by virtue of this, it is made possible to identify the synchronization signal transmitter 2 regardless of whether or not the imaging apparatus 3 has a radio wave transmission function (even when it only includes a reception function).

On the other hand, the bulb controller 12a of the radiation control device has the function of acquiring the identification information via the communicator 12b from the synchronization signal transmitter 2 connected by wired connection.

Also, the bulb controller 12a has the function of receiving, via the communicator 12b, the identification information that has been transferred by the imaging apparatus 3.

Also, the bulb controller 12a has the function for determining whether or not the identification information that has been acquired by the controller itself and the identification information which the imaging apparatus 3 has received (transferred) are in agreement with each other.

It should be noted that, with regard to the point in time to perform the determination, the determination is to be performed when the irradiation apparatus 1 and the imaging apparatus 3 need to operate in synchronization with each other, for example, immediately before the imaging (radiation irradiation) is started (e.g., in response to the exposure switch 15a being pressed) or while the kymography is being performed.

Use of the radiation imaging system 100 of this embodiment having the above-described features makes it possible to determine whether or not the irradiation apparatus 1 and the imaging apparatus 3 are successful in receiving the synchronization signal from the same synchronization signal transmitter 2 even when multiple synchronization signal transmitters 2 exist, i.e., even when a wireless network having the same ESSID and the same access key exists near the system.

Second Embodiment

Next, the second embodiment of the present invention will be described below. It should be noted that in the following descriptions and illustrations, the same features as those in the first embodiment are indicated by the same reference signs and explanations thereof will not be repeated.

In the imaging system 100 according to the above-described first embodiment, the imaging apparatus 3 is responsible for the determination of whether or not the identification information that has been received by the irradiation apparatus 1 and the identification information that has been received by the imaging apparatus 3 are in agreement with each other. Meanwhile, in the radiation imaging system 100A according to this embodiment, the same determination is performed by the radiation imaging apparatus (hereinafter referred to as "imaging apparatus 3A").

Hence, the radiation irradiation apparatus (hereinafter referred to as "irradiation apparatus 1A") and the imaging apparatus 3A according to this embodiment differ from the irradiation apparatus 1 and the imaging apparatus 3 according to the first embodiment, respectively.

For example, the storage device of the radiation control device 12A and the storage device 35 of the imaging apparatus 3 of this embodiment store processing programs the content (to be later described in detail) of which is partly different from the first embodiment.

Hence, the controller of the radiation control device 12A and the panel controller 31 of the imaging apparatus 3A of this embodiment perform the following operations that are different than those in the first embodiment.

Specifically, the bulb controller 12a of the radiation control device 12A has the function of acquiring the identification information from the synchronization signal transmitter 2 connected by wired connection via the communicator 12b and transferring it to the imaging apparatus 3A.

On the other hand, the panel controller 31 of the imaging apparatus 3A has the function of receiving, via the communicator 34, the identification information from the synchronization signal transmitter 2 near the system.

Also, the panel controller 31 has the function of receiving, via the communicator 34, the identification information that has been transferred by the irradiation apparatus 1.

Also, the panel controller 31 has the function for determining whether or not the identification information which the irradiation apparatus 1 has obtained (or transferred) and the identification information that has been received by the controller itself are in agreement with each other.

Use of the radiation imaging system 100 of this embodiment having the above-described features makes it possible to determine whether or not the irradiation apparatus 1 and the imaging apparatus 3 are successful in receiving the synchronization signal from the same synchronization signal transmitter 2 in the same manner as in the first embodiment even when multiple synchronization signal transmitters 2 exists.

It should be noted that, in the above-described first and second embodiments, when the wired network interconnecting the radiation control device 12 and the synchronization signal transmitter 2 has a closed configuration segregated from external networks, the determination of whether or not the pieces of identification information are in agreement with each other may not be performed and it may be determined that the irradiation apparatus 1 and the imaging apparatus 3 have been connected to the same synchronization signal transmitter 2 when the imaging apparatus 3 has been connected to the synchronization signal transmitter 2.

Figure 8:
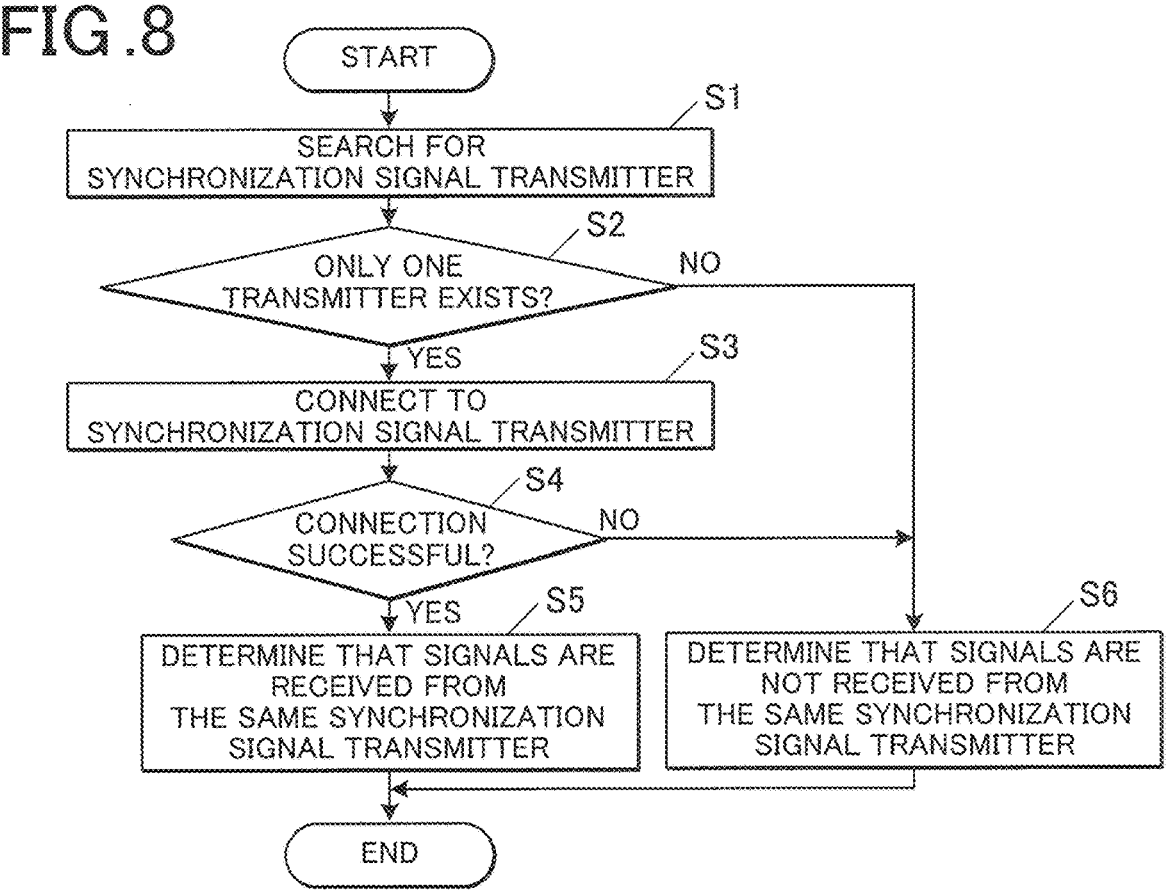
FIG. 8 is a flowchart illustrating the processing performed by the radiation imaging system of FIG. 1.

Specifically, the bulb controller 12a of the irradiation apparatus 1 or the panel controller 31 of the imaging apparatus 3 is to perform the processing, for example, as illustrated in FIG. 8.

First, the synchronization signal transmitter 2 is searched for (step S1) to determine whether or not one single synchronization signal transmitter 2 that can be a target of connection exists (step S2). Here, when it has been determined that only one target exists (Yes in the step S2), then the system is connected to the synchronization signal transmitter 2 (step S3) and determination is made on whether or not the connection has been successful (step S4). Here, when it has been determined that the connection has been successful (Yes in the step S4), then it is determined that a state is entered where the irradiation apparatus 1 and the imaging apparatus 3 refer to the synchronization signal of the same synchronization signal transmitter 2. On the other hand, when it has been determined in the step S2 that the target is not the only one that exists (No in the step S2) or when it has been determined in the step S4 that the connection was not successful (No in the step S4), then it is determined that a state is not entered where the irradiation apparatus 1 and the imaging apparatus 3 refer to the synchronization signal of the same synchronization signal transmitter 2, and the above-described determination is also made regarding whether or not the pieces of identification information are in agreement with each other.

Third Embodiment

Next, the third embodiment of the present invention will be described below. It should be noted that, in the following descriptions and illustrations, the same features as those in the first and second embodiments are indicated by the same reference signs and explanations thereof will not be repeated.

In the imaging systems 100, 100A according to the above-described first and second embodiments, either of the irradiation apparatus 1 and the imaging apparatus 3 is responsible for the determination of whether or not the identification information that has been received by the irradiation apparatus 1 and the identification information that has been received by the imaging apparatus 3 are in agreement with each other. Meanwhile, in the radiation imaging system 100 according to this embodiment, this determination is performed by the irradiation apparatus 1 and the imaging apparatus 3, respectively.

Hence, the irradiation apparatus 1 and the imaging apparatus 3 according to this embodiment differ from the irradiation apparatuses 1, 1A and the imaging apparatuses 3, 3A according to the first and second embodiments, respectively.

For example, the storage device 12c of the radiation control device 12A and the storage device 35 of the imaging apparatus 3 according to this embodiment store in advance the identification information held by the synchronization signal transmitter 2 to which the system should maintain connection.

Also, the storage device 12c of the radiation control device 12A and the storage device 35 of the imaging apparatus 3 store processing programs the content (to be later described in detail) of which is partly different from the first embodiment.

Hence, the controller of the radiation control device 12 and the panel controller 31 of the imaging apparatus 3 according to this embodiment perform the following operations different than those in the first and second embodiments.

The bulb controller 12a has the function for determining whether or not the identification information that has been acquired by the controller itself and the identification information stored in advance in the controller itself are in agreement with each other.

Also, the panel controller 31 has the function for determining whether or not the identification information that has been acquired by the controller itself and the identification information stored in advance in the controller itself are in agreement with each other.

Use of the radiation imaging system 100 of this embodiment having the above-described features makes it possible to determine whether or not the irradiation apparatus 1 and the imaging apparatus 3 are successful in receiving the synchronization signal from the same synchronization signal transmitter 2 in the same manner as in the first and second embodiments even when multiple synchronization signal transmitters 2 exists.

Fourth Embodiment

Figure 9:
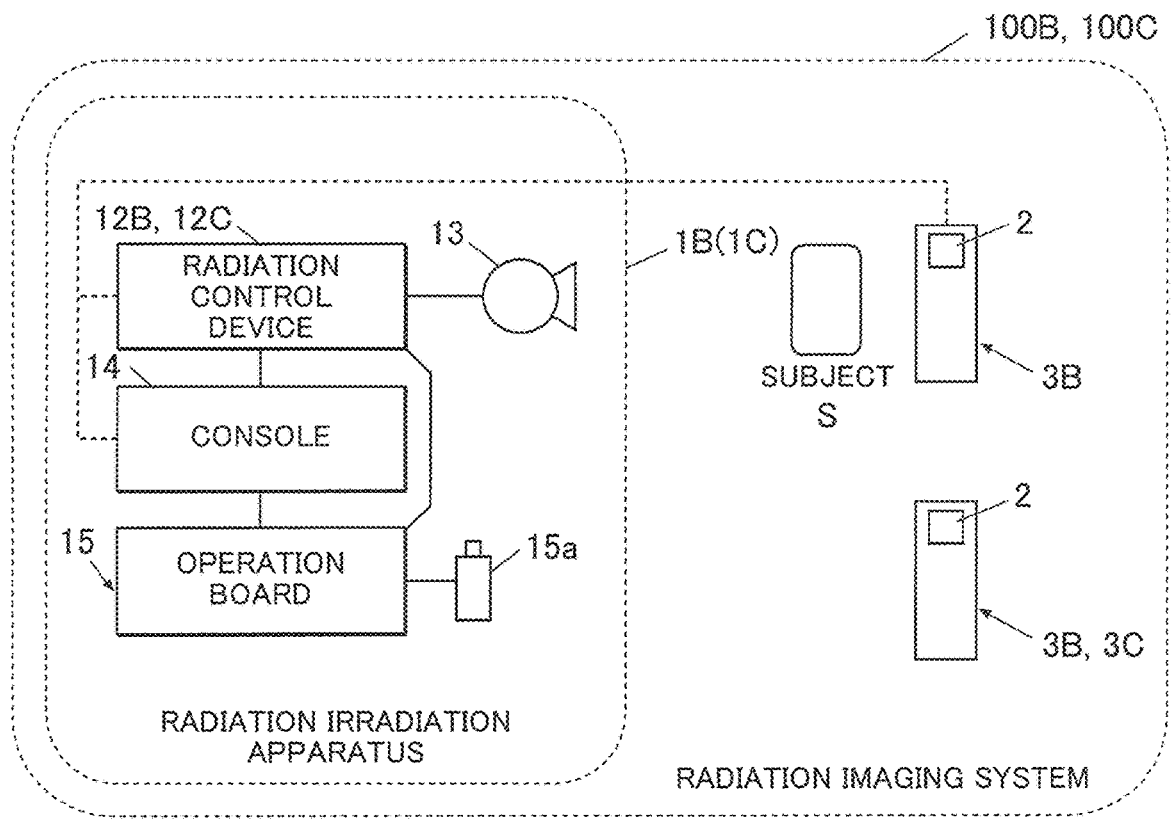
FIG. 9 is a block diagram illustrating a schematic configuration of the radiation imaging system according to fourth to sixth embodiments of the present invention.

Next, the fourth embodiment of the present invention will be described. FIG. 9 is a block diagram that illustrates the schematic configuration of the radiation imaging system 100B according to the fourth embodiment of the present invention.

It should be noted that, in the following descriptions and illustrations, the same features as those in the first embodiment are indicated by the same reference signs and explanations thereof will not be repeated.

Whilst the radiation imaging system 100B according to the above-described first embodiment has the synchronization signal transmitter 2 which is connected to the irradiation apparatus 1 by wired connection or incorporated in the irradiation apparatus 1, the radiation imaging system 100B according to this embodiment has the synchronization signal transmitter 2 which is incorporated in a radiation imaging apparatus (hereinafter referred to as "imaging apparatus 3B") as illustrated in FIG. 9 such that the irradiation apparatus 1 and the synchronization signal transmitter 2 perform wireless communications.

As a result, the radiation irradiation apparatus (hereinafter referred to as "irradiation apparatus 1B") and the imaging apparatus 3B according to this embodiment differ from the irradiation apparatus 1 and the imaging apparatus 3 according to the first embodiment, respectively.

Figure 10:
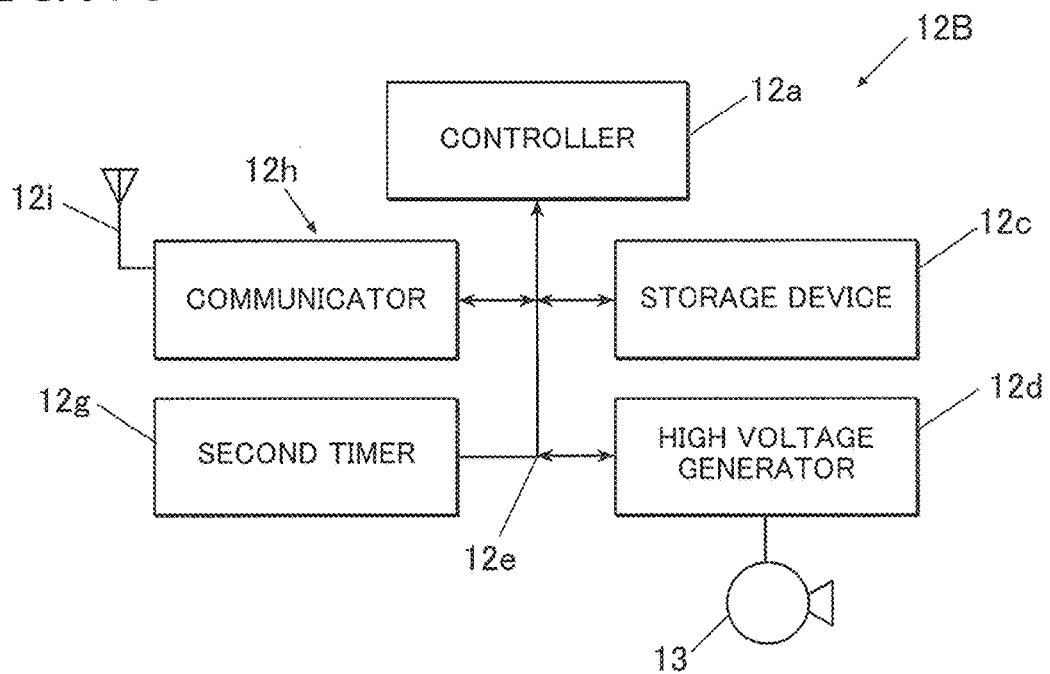
FIG. 10 is a block diagram illustrating a specific configuration of a radiation control device provided in the radiation imaging system of FIG. 9.

Specifically, as illustrated in FIG. 10, the radiation control device 12B includes a second timer 12g.

Also, the communicator 12h of the radiation control device 12B includes a wireless communication interface and an antenna 12i for performing transmission and reception of radio waves with the synchronization signal transmitter 2.

Figure 11:
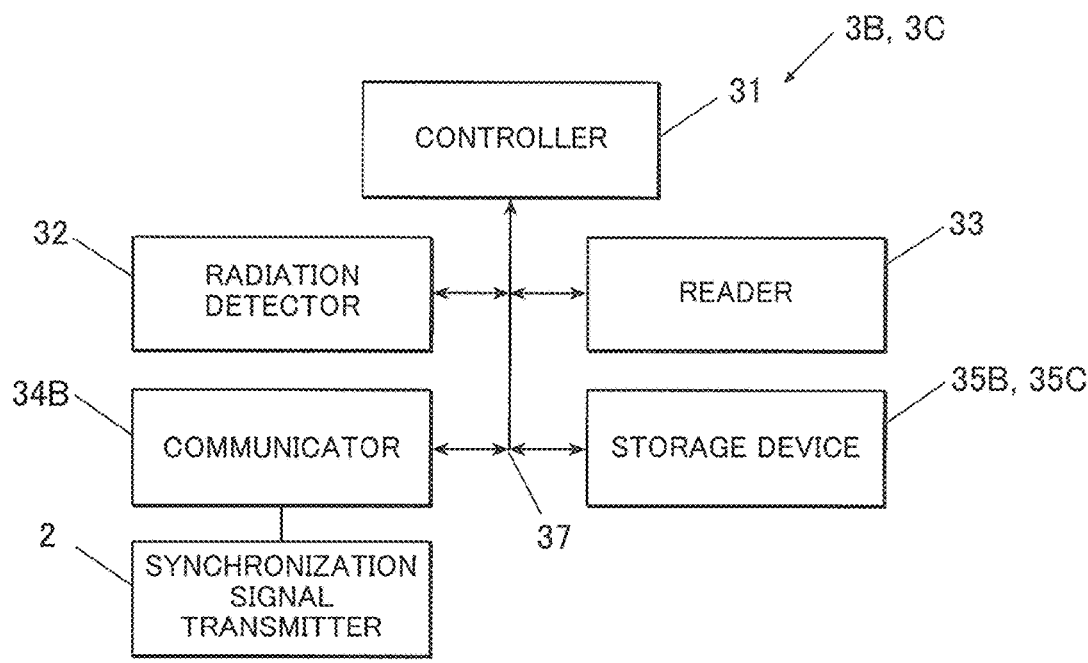
FIG. 11 is a block diagram illustrating the specific configuration of a radiation imaging apparatus provided in the radiation imaging system of FIG. 9.

Also, as illustrated in FIG. 11, the imaging apparatus 3B does not have a feature that corresponds to the second timer 36 of the first embodiment.

Also, the communicator 12h of the imaging apparatus 3B includes a wired communication interface and connected to the synchronization signal transmitter 2 by wired connection.

When the wireless communications in accordance with IEEE 802.11 are to be performed by the radiation imaging system according to this embodiment, the irradiation apparatus 1 should correspond to the above-described terminal.

In other words, the count value of the first timer 21 included in the beacon will be acquired every time the bulb controller 12a of the irradiation apparatus 1 receives the beacon.

In addition, the bulb controller 12a of the irradiation apparatus 1 causes the count value of the second timer 12g provided in the irradiation apparatus 1 as such to be adjusted to correspond to the acquired count value of the first timer.

Also, the storage device of the radiation control device 12B and the storage device 35 of the imaging apparatus 3B according to this embodiment store processing programs the content (to be later described in detail) of which is partly different from the first embodiment.

Hence, the controller of the radiation control device 12B and the panel controller 31 of the imaging apparatus 3B according to this embodiment perform the following operations that are different than those in the first embodiment.

Specifically, the panel controller 31 of the imaging apparatus 3B has the function of acquiring the identification information from the built-in synchronization signal transmitter 2 via the communicator 34 and transferring it to the irradiation apparatus 1.

On the other hand, the bulb controller 12a of the radiation control device 12 has the function of receiving, via the communicator 12b, the identification information from the synchronization signal transmitter 2 around the system.

At this point, the radiation control device 12 may receive the identification information from the synchronization signal transmitter 2 to which the system is connected or may receive it from an unconnected access point existing in the surrounding area.

By this configuration, it is made possible to use an unconnected access point as the synchronization signal transmitter 2. Also, by virtue of this, it is made possible to identify the synchronization signal transmitter 2 regardless of whether or not the radiation control device 12 has a radio wave transmission function (even when it only includes a reception function).

Also, the bulb controller 12a has the function of receiving, via the communicator 12b, the identification information that has been transferred by the imaging apparatus 3B.

Also, the bulb controller 12a has the function for determining whether or not the identification information that has been received by the controller itself and the identification information which the imaging apparatus 3 has acquired (transferred) are in agreement with each other.

Use of the radiation imaging system 100B of this embodiment having the above-described features makes it possible to determine whether or not the irradiation apparatus 1 and the imaging apparatus 3 are successful in receiving the synchronization signal from the same synchronization signal transmitter 2 in the same manner as in the first embodiment even when multiple synchronization signal transmitters 2 exists.

Fifth Embodiment

Next, the fifth embodiment of the present invention will be described below. It should be noted that, in the following descriptions and illustrations, the same features as those in the fourth embodiment are indicated by the same reference signs and explanations thereof will not be repeated.

In the imaging system 100B according to the above-described fourth embodiment, the imaging apparatus 3B is responsible for the determination of whether or not the identification information that has been received by the irradiation apparatus 1 and the identification information that has been received by the imaging apparatus 3 are in agreement with each other. Meanwhile, in the radiation imaging system 100C according to this embodiment, this determination is performed by the radiation imaging apparatus (hereinafter referred to as "imaging apparatus 3C").

Hence, the radiation irradiation apparatus (hereinafter referred to as "irradiation apparatus 1C") and the imaging apparatus 3C according to this embodiment differ from the irradiation apparatus 1B and the imaging apparatus 3B according to the fourth embodiment, respectively.

For example, the storage device 12c of the radiation control device 12A and the storage device 35C of the imaging apparatus 3 of this embodiment store processing programs the content (to be later described in detail) of which is partly different from the fourth embodiment.

Hence, the bulb controller 12a of the radiation control device 12A and the panel controller 31 of the imaging apparatus 3A according to this embodiment perform the following operations that are different than those in the first embodiment.

Specifically, the bulb controller 12a of the radiation control device 12A has the function of receiving the identification information from the synchronization signal transmitter 2 near the system via the communicator 12b and transferring it to the imaging apparatus 3A.

On the other hand, the panel controller 31 of the imaging apparatus 3A has the function of acquiring, via the communicator 34, the identification information from the built-in synchronization signal transmitter 2.

Also, the panel controller 31 has the function of receiving the identification information which the irradiation apparatus 1 has received (transferred), the identification information being received via the communicator 34 from the irradiation apparatus 1.

In addition, the panel controller 31 has the function for determining whether or not the identification information that has been received by the irradiation apparatus 1 and the identification information that has been received by the controller itself are in agreement with each other.

Use of the radiation imaging system 100C of this embodiment having the above-described features makes it possible to determine whether or not the irradiation apparatus 1 and the imaging apparatus 3 are successful in receiving the synchronization signal from the same synchronization signal transmitter 2 in the same manner as in the fourth embodiment even when multiple synchronization signal transmitters 2 exists.

Sixth Embodiment

Next, the sixth embodiment of the present invention will be described. It should be noted that, in the following descriptions and illustrations, the same features as those in the fourth and fifth embodiments are indicated by the same reference signs and explanations thereof will not be repeated.

In the imaging system 100B according to above-described fourth and fifth embodiments, either of the irradiation apparatus 1B and the imaging apparatus 3B is responsible for the determination of whether or not the identification information that has been received by the irradiation apparatus 1B and the identification information that has been received by the imaging apparatus 3B are in agreement with each other. Meanwhile, in the radiation imaging system 100B according to this embodiment, this determination is performed by the irradiation apparatus 1B and the imaging apparatus 3B, respectively.

Hence, the irradiation apparatus 1B and the imaging apparatus 3B according to this embodiment differ from the irradiation apparatuses 1B, 1C and the imaging apparatuses 3B, 3C according to the fourth and fifth embodiments, respectively.

For example, the storage device 12c of the radiation control device 12B and the storage device 35 of the imaging apparatus 3 of this embodiment store in advance the identification information held by the synchronization signal transmitter 2 to which the system should maintain connection.

Also, the storage device 12c of the radiation control device 12B and the storage device 35 of the imaging apparatus 3B of this embodiment store processing programs the content (to be later described in detail) of which is partly different from the first embodiment.

Hence, the controller of the radiation control device 12B and the panel controller 31 of the imaging apparatus 3B of this embodiment perform the following operations that are different than those in the fourth and fifth embodiments.

The bulb controller 12a has the function for determining whether or not the identification information that has been acquired by the controller itself and the identification information stored in advance in the controller itself are in agreement with each other.

Also, the panel controller 31 has the function for determining whether or not the identification information that has been acquired by the controller itself and the identification information stored in advance in the controller itself are in agreement with each other.

Use of the radiation imaging system 100B of this embodiment having the above-described features makes it possible to determine whether or not the irradiation apparatus 1 and the imaging apparatus 3 are successful in receiving the synchronization signal from the same synchronization signal transmitter 2 in the same manner as in the fourth and fifth embodiments even when multiple synchronization signal transmitters 2 exists.

It should be noted that, in the above-described first to sixth embodiments, the radiation imaging systems 100 to 100C have been described in which either of the communication between the irradiation apparatuses 1 to 1C and the synchronization signal transmitter 2 and the communication between the synchronization signal transmitter 2 and the imaging apparatuses 3 to 3C is wired communication and the other is wireless communication. Meanwhile, it is also possible to configure the system such that the communication between the irradiation apparatuses 1 to 1C and the synchronization signal transmitter 2 and the communication between the synchronization signal transmitter 2 and the imaging apparatuses 3 to 3C are both performed as wireless communications.

Also, in the above-described first to sixth embodiments, explanations have been provided based on the examples where the synchronization signal transmitter 2 is connected to both the radiation control devices 12 to 12C and the console 14. Meanwhile, the mode of connection of the present invention is not limited to this specific one and it is also envisaged that the synchronization signal transmitter 2 is only connected to the radiation control devices 12 to 12C or the connection is only established between the synchronization signal transmitter 2 and the console 14.

Since the irradiation apparatus 1 is a device that emits radiation, direct interconnection of the synchronization signal transmitter 2 and the radiation control devices 12 to 12C makes it possible to control the timing of radiation irradiation more accurately.

On the other hand, since the console 14 is a device that controls the entire imaging system 100, direct interconnection of the synchronization signal transmitter 2 and the console 14 makes it possible to perform processes such as synchronization confirmation efficiently by the console 14.

EXAMPLE 1

Next, a new problem that may arise as a result of implementation of the present invention as illustrated in the above-described embodiments will be described below along with the specific examples of implementation for solving the new problem.

EXAMPLE 1-1

In the radiation imaging system according to the above-described embodiment, if it is not possible to recognize the result of the determination of whether or not the identification information that has been received by the irradiation apparatus 1 and the identification information that has been received by the imaging apparatus 3 are in agreement with each other, then it is possible that the kymography is started in a state where the irradiation apparatus 1 and the imaging apparatus 3 refer to different synchronization signals (hereinafter referred to as "out-of-synchronization state"). When the kymography is performed in the out-of-synchronization state, the re-imaging is performed while some pieces of image data cannot be successfully generated, as a result of which the subject may be unnecessarily exposed to the radiation.

In view of such a problem, the imaging may be performed only when the pieces of identification information are in agreement with each other. Specifically, the bulb controller 12a of the irradiation apparatus 1 or the panel controller 31 of the imaging apparatus 3 is to perform the processing, for example, illustrated in FIG. 12.

First, determination is made on whether or not the identification information that has been received by the irradiation apparatus 1 and the identification information that has been received by the imaging apparatus 3 are in agreement with each other (step S11) and, if it has been determined that they are in agreement with each other (Yes in the step S11), the radiation irradiation by the irradiation apparatus 1 is permitted (step S12), and the various subsequent processes (step S13) continue to be performed. Meanwhile, if it has been determined that they are not in agreement with each other in the step S1 (No in the step S11), the processes at the time of non-agreement (non-permission of radiation irradiation and notification of the fact of the out-of-synchronization state in the step S14) are to be performed.

By this configuration, since it is not possible to perform the imaging in the out-of-synchronization state, it is made possible to prevent unnecessary exposure of the subject to be tested to the radiation due to the re-imaging.

EXAMPLE 1-2

Also, the fact that the pieces of identification information are in agreement with each other may be notified to the user in view of the problem mentioned in the above-described Example 1-1 that it is possible that the kymography is started in the out-of-synchronization state if it is not possible to recognize the result of the determination of whether or not the identification information that has been received by the irradiation apparatus 1 and the identification information that has been received by the imaging apparatus 3 are in agreement with each other. Specifically, the bulb controller 12a of the irradiation apparatus 1 or the panel controller 31 of the imaging apparatus 3 is to perform the processing, for example, illustrated in FIG. 13.

First, determination is made on whether or not the identification information that has been received by the irradiation apparatus 1 and the identification information that has been received by the imaging apparatus 3 are in agreement with each other (step S21). If it has been determined that they are in agreement with each other (Yes in the step S21), the fact that the out-of-synchronization state is not entered is notified (step S22A) and the various subsequent processes (step S23) continue to be performed. Meanwhile, if it has been determined that they are not in agreement with each other in the step S21 (No in the step S21), then the processes at the time of non-agreement (non-permission of radiation irradiation and notification of the fact of the out-of-synchronization state) are to be performed.

The notification may be provided using indication, sound, vibration, etc.

The communicator that provides the notification may be provided in the irradiation apparatus 1 and the imaging apparatus 3 or may be provided in another device such as the console.

By this configuration, a user can confirm the fact that the irradiation apparatus 1 and the imaging apparatus 3 refer to the synchronization signal of the same synchronization signal transmitter 2, so that it is made possible to prevent unnecessary exposure of the subject to be tested to the radiation due to the re-imaging.

EXAMPLE 1-3

In the radiation imaging system according to the above-described embodiment, after it has been determined that the out-of-synchronization state is not entered, it is possible that the synchronization signal transmitter 2 may be mishandled and confused with another one due to change in the wireless environment (e.g., change in the wireless channel by DFS (Dynamic Frequency Selection)). When the synchronization signal generator is mishandled and confused with another one, the mishandling and confusion leads to entry into the out-of-synchronization state and failure in the kymography, as a result of which re-imaging is necessitated and the subject will be unnecessarily exposed to the radiation.

Figure 14:
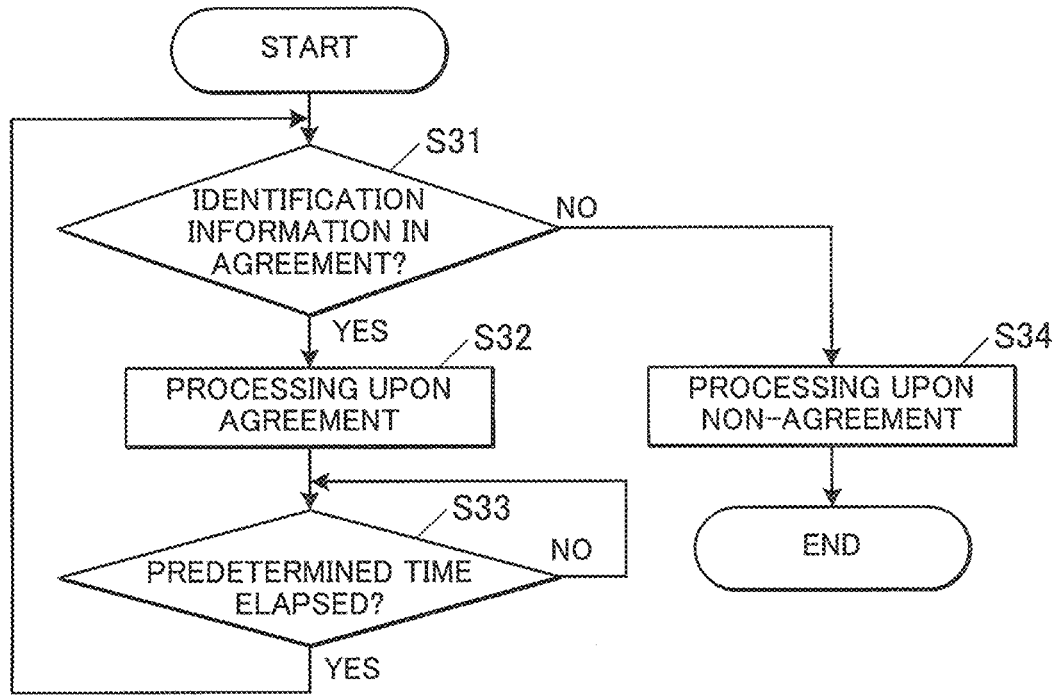
FIG. 14 is a flowchart illustrating the processing performed by the radiation imaging system according to Example 1-3.

In view of such a problem, whether or not the pieces of identification information are in agreement with each other may be periodically monitored. Specifically, the bulb controller 12a of the irradiation apparatus 1 or the panel controller 31 of the imaging apparatus 3 is to perform the processing, for example, illustrated in FIG. 14.

First, determination is made on whether or not the identification information that has been received by the irradiation apparatus 1 and the identification information that has been received by the imaging apparatus 3 are in agreement with each other (step S31) and, if it has been determined that they are in agreement with each other (Yes in the step S31), then the processes at the time of the agreement (permission of radiation irradiation and the notification of the fact that the pieces of identification information are in agreement with each other in the step S32) are performed. In addition, after a predetermined period of time has elapsed since the previous determination (Yes in the step S33), the process goes back to the process of the step S1. Meanwhile, if it has been determined that they are not in agreement with each other in the step S31 (No in the step S31), the processes at the time of non-agreement (non-permission of radiation irradiation and notification of the fact of the out-of-synchronization state in the step S34) are to be performed.

By this configuration, mishandling and confusion of the synchronization signal transmitter 2 can be prevented and the reliability of the system can be enhanced.

Also, the restoration processing upon occurrence of the out-of-synchronization state can be promptly performed.

In addition, since it is made easier to perform the restoration while the degree of the out-of-synchronization falls within an allowable range, it is made possible to lower the probability that the subject is unnecessarily exposed to the radiation because of the re-imaging.

EXAMPLE 1-4

Figure 12:
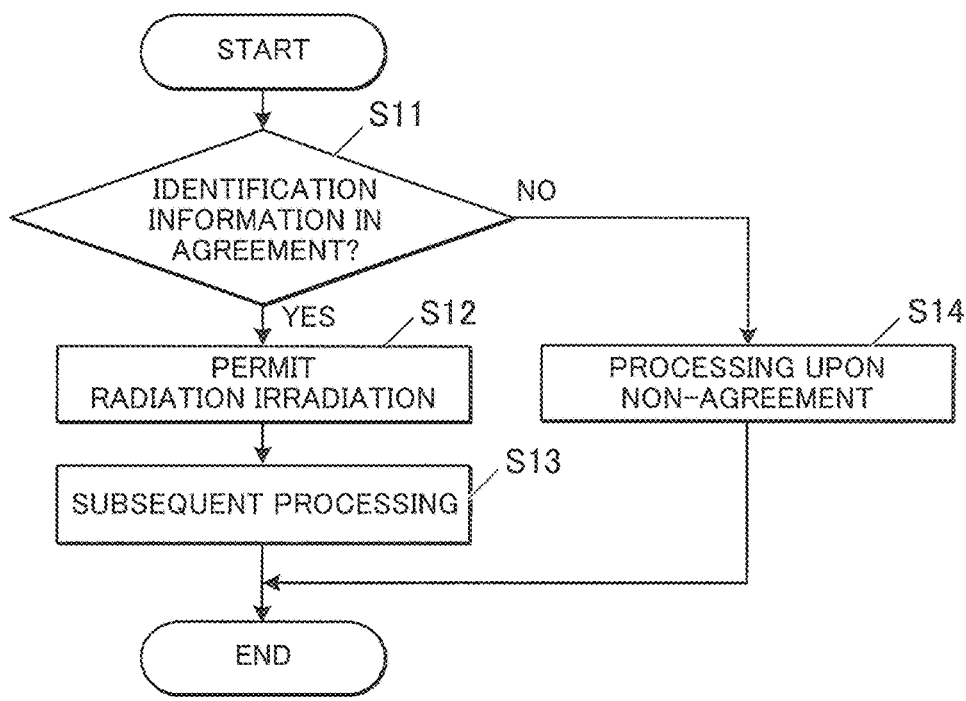
FIG. 12 is a flowchart illustrating the processing performed by the radiation imaging system according to Example 1-1.
Figure 13:
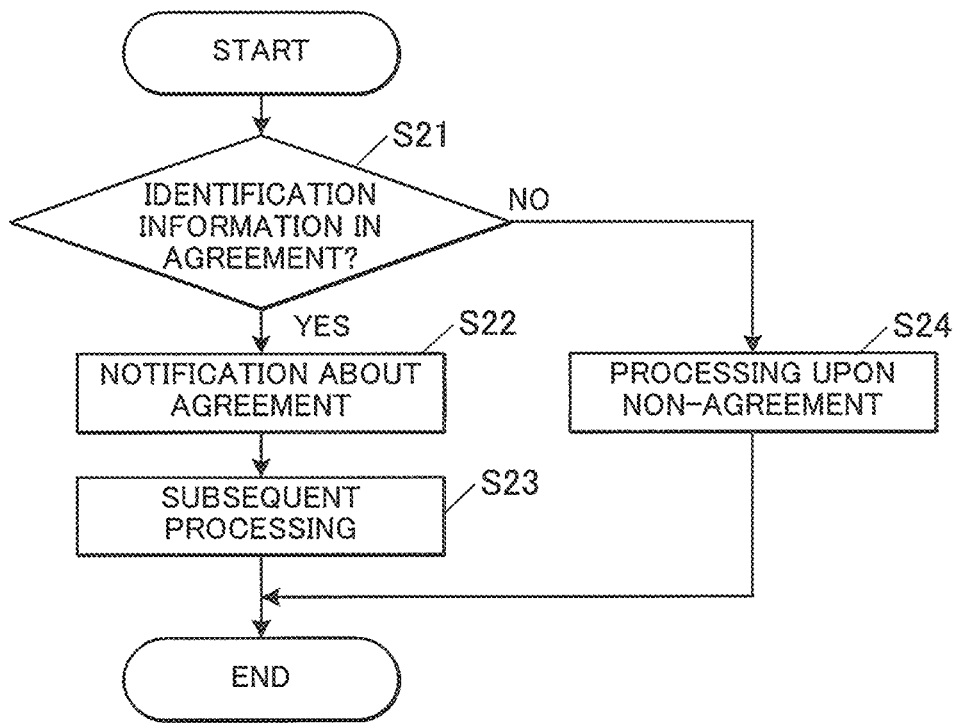
FIG. 13 is a flowchart illustrating the processing performed by the radiation imaging system according to Example 1-2.

In view of the problem mentioned in the above-described Example 1-3 that it is possible that the synchronization signal transmitter 2 may be mishandled and confused with another one due to change in the wireless environment even after it has been determined that the pieces of identification information are in agreement with each other, whether or not the pieces of identification information are in agreement with each other may be confirmed when the wireless connection between the synchronization signal transmitter 2 and the irradiation apparatus 1 or the imaging apparatus 3 is disconnected because of a certain reason (the beacon cannot be received and the synchronization signal transmitter 2 is lost sight of; forcible disconnection from the synchronization signal transmitter 2, etc.) and reconnection is made thereto afterward. Specifically, the processing illustrated in FIG. 12 or FIG. 13 are to be performed after the re-connection processing was made.

By this implementation as well, in the same manner as in the above-described Example 1-3, mishandling and confusion of the synchronization signal transmitter 2 can be prevented and the reliability of the system can be enhanced.

Also, the restoration processing upon occurrence of the out-of-synchronization state can be promptly performed.

In addition, since it is made easier to perform the restoration while the degree of the out-of-synchronization falls within an allowable range, it is made possible to lower the probability that the subject is unnecessarily exposed to the radiation because of the re-imaging.

EXAMPLE 1-5

In the above-described Example 1-3, the determination of whether or not the predetermined period of time elapsed after the previous determination (step S33) may be replaced by, for example, determination of whether or not wireless reconnection has been detected, or the determination of whether or not the gap of the synchronization signals has been detected.

By this implementation as well, in the same manner as in the above-described Example 1-3, mishandling and confusion of the synchronization signal transmitter 2 can be prevented and the reliability of the system can be enhanced.

Also, the restoration processing upon occurrence of the out-of-synchronization state can be promptly performed.

In addition, since it is made easier to perform the restoration while the degree of the out-of-synchronization falls within an allowable range, it is made possible to lower the probability that the subject is unnecessarily exposed to the radiation because of the re-imaging.

EXAMPLE 1-6

Figure 15:
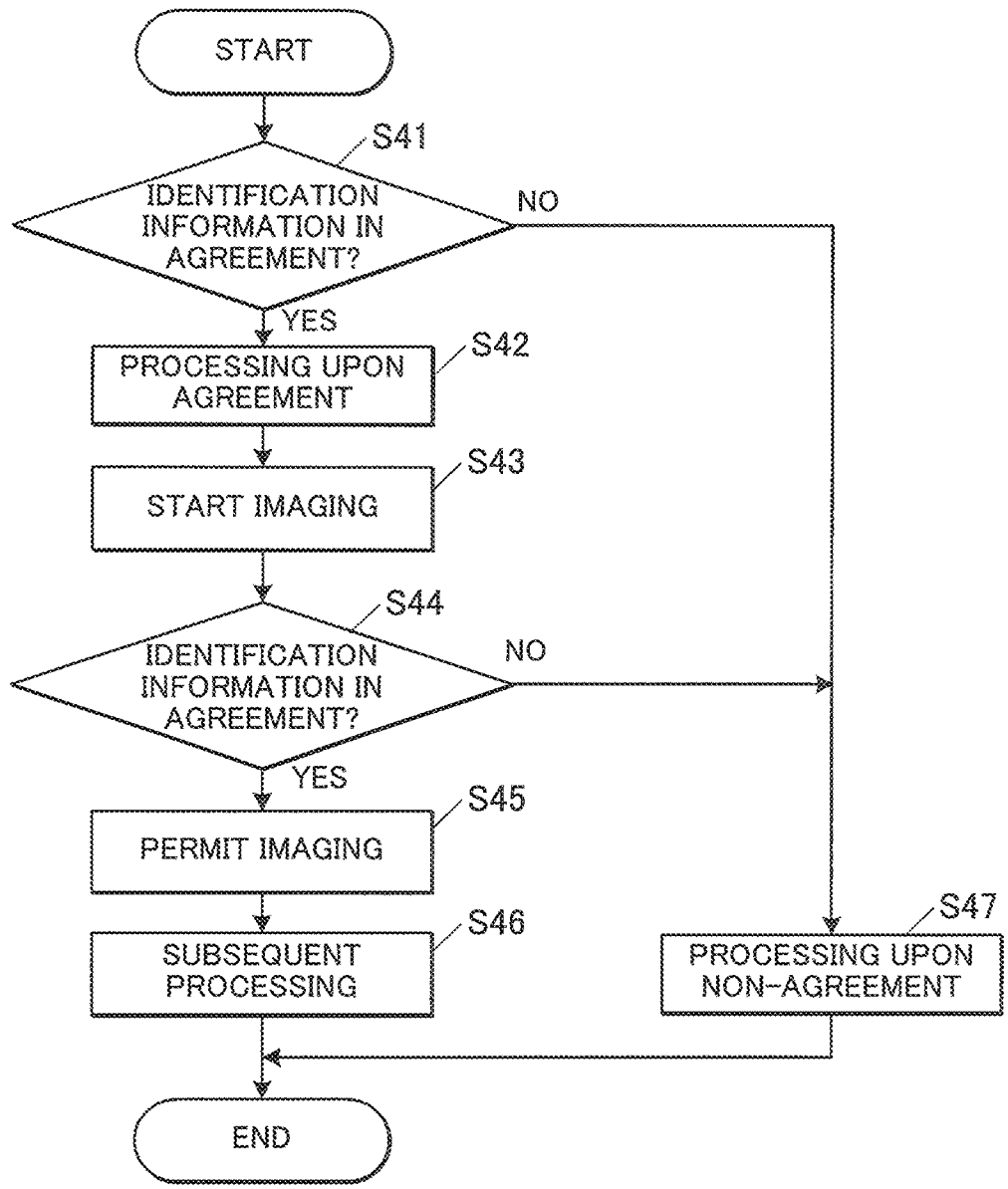
FIG. 15 is a flowchart illustrating the processing performed by the radiation imaging system according to Example 1-6.

In view of the problem mentioned in the above-described Example 1-3 that, it is possible that the synchronization signal transmitter 2 may be mishandled and confused with another one due to change in the wireless environment after it has been determined that the pieces of the identification information are in agreement with each other, whether or not the pieces of identification information are in agreement with each other may be confirmed again at the time of start of the imaging. Specifically, the bulb controller 12a of the irradiation apparatus 1 or the panel controller 31 of the imaging apparatus 3 is to perform, for example, the processing illustrated in FIG. 15.

First, when the determination is affirmative in the determination prior to the imaging that the pieces of identification information are in agreement with each other (step S41) and the various processes at the time of agreement have been performed (step S42) and the imaging is started (the exposure switch 15a is pressed) (step S43), then the determination of whether or not the pieces of identification information are in agreement with each other is performed again (step S44). If it has been determined that they are in agreement with each other (Yes in the step S44), the imaging (exposure to radiation) is permitted (step S45) and the various processes at the time of agreement are performed (step S46). Meanwhile, if it has been determined in the steps S41 and S44 that the pieces of identification information are not in agreement with each other (No in the steps S41, S44), then the processes at the time of non-agreement (non-permission of radiation irradiation and notification of the fact of the out-of-synchronization state, the step S47) are performed.

By this configuration, through the confirmation of the validity of the connection immediately before the start of the imaging, it is made possible to prevent occurrence of the out-of-synchronization state and the subject to be tested can be protected from being unnecessarily exposed to the radiation because of the re-imaging.

EXAMPLE 2-1

Figure 16:
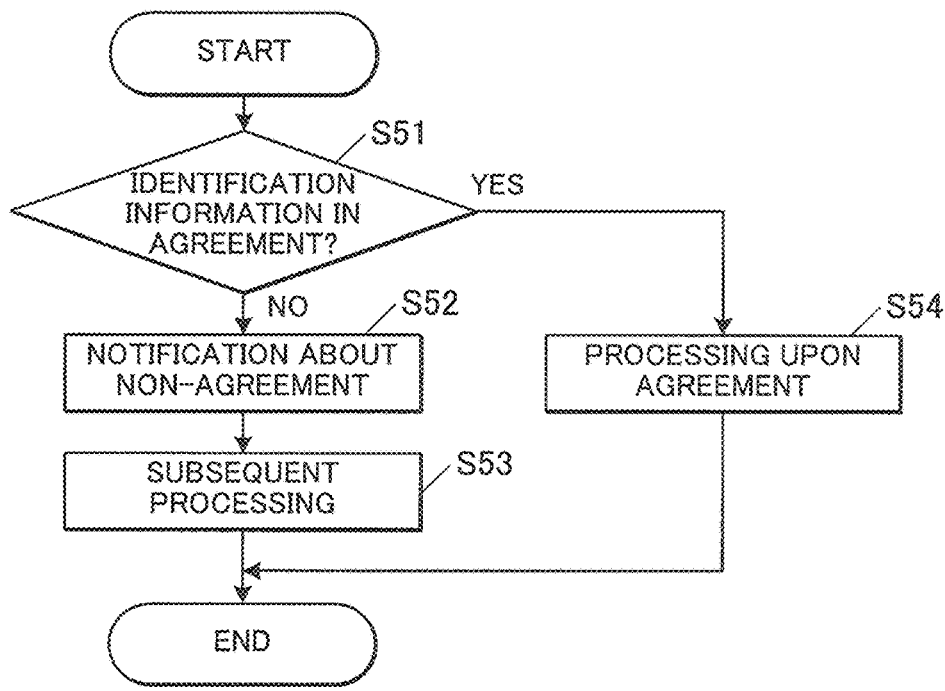
FIG. 16 is a flowchart illustrating the processing performed by the radiation imaging system according to Example 2-1.

Also, in view of the problem mentioned in the above-described Example 1-1 that it is possible that the kymography is started in the out-of-synchronization state if it is not possible to recognize the result of the determination of whether or not the identification information that has been received by the irradiation apparatus 1 and the identification information that has been received by the imaging apparatus 3 are in agreement with each other, the fact of non-agreement of the identification information may be notified to the user. Specifically, the bulb controller 12a of the irradiation apparatus 1 or the panel controller 31 of the imaging apparatus 3 is to perform the processing, for example, illustrated in FIG. 16.

First, it is determined the identification information that has been received by the irradiation apparatus 1 and the identification information that has been received by the imaging apparatus 3 are in agreement with each other (step S51). If it has been determined that that they are not in agreement with each other (No in the step S51), then the fact of the non-agreement is notified (step S52) and the processes at the time of non-agreement (non-permission of radiation irradiation and notification of the fact of the out-of-synchronization state, the step S53) are to be performed. Meanwhile, if it has been determined in the step S1 that they are in agreement with each other (Yes in the step S51), then the various processes at the time of the agreement (step S54) continue to be performed.

The notification may be provided using indication, sound, vibration, etc.

The communicator that provides the notification may be provided in the irradiation apparatus 1 and the imaging apparatus 3 or may be provided in another device such as the console.

By this configuration, since the user is allowed to confirm the fact that the irradiation apparatus 1 and the imaging apparatus 3 do not refer to the synchronization signal of the same synchronization signal transmitter 2, it is made possible to prevent unnecessary exposure of the subject to be tested to the radiation due to the re-imaging.

EXAMPLE 2-2

In the radiation imaging system according to the above-described embodiment, it is possible that the synchronization signal transmitter 2 as the target on which whether or not the pieces of identification information are in agreement with each other should be determined cannot be found due to wireless radio wave failure and environmental deficiency (e.g., DFS occurred and transmission of radio waves is stopped) or the like.

Figure 17:
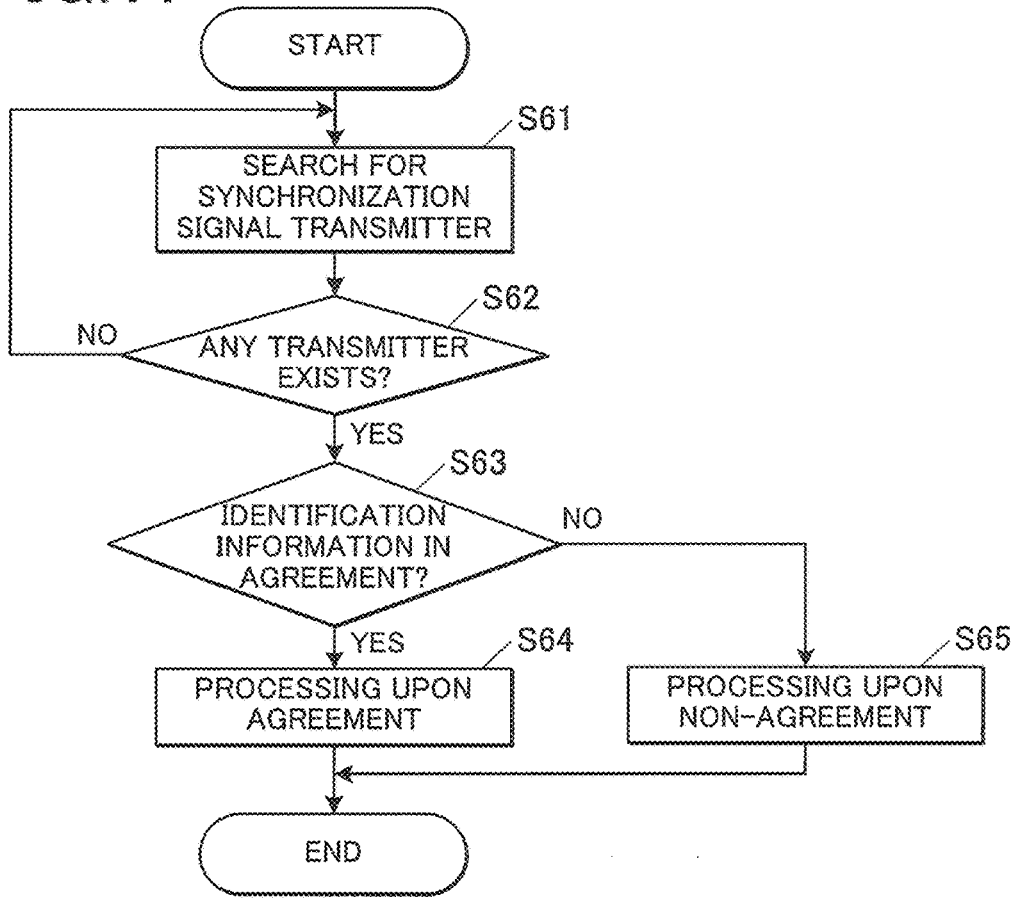
FIG. 17 is a flowchart illustrating the processing performed by the radiation imaging system according to Example 2-2.

In view of such a problem, when no candidate for the synchronization signal transmitter 2 can be found, the synchronization signal transmitter 2 is again searched for, and the identification processing may be performed when it has been found. Specifically, the bulb controller 12a of the irradiation apparatus 1 or the panel controller 31 of the imaging apparatus 3 is to perform, for example, the processing illustrated in FIG. 17.

First, the synchronization signal transmitter 2 is searched for (step S61) and determination is made on whether or not any synchronization signal transmitter 2 as a target of connection exists (step S62). Here, if it has been determined that the target exists (Yes in the step S62), then determination is made on whether or not the pieces of identification information are in agreement with each other (step S63). Here, if it has been determined that the pieces of identification information are in agreement with each other (Yes in the step S63), the processes at the time of the agreement (permission of radiation irradiation and the notification of the fact that the pieces of identification information are in agreement with each other in the step S64) are to be performed. Meanwhile, if it has been determined in the step S3 that the pieces of identification information are not in agreement with each other (No in the step S3), then the processes at the time of non-agreement (non-permission of radiation irradiation and notification of the fact of the out-of-synchronization state, the step S65) are to be performed.

By this configuration, the restoration at the time of occurrence of an abnormality can be promptly performed.

Also, the robustness to the environment can be enhanced.

EXAMPLE 2-3

In the radiation imaging system according to the above-described embodiment, it is possible that the synchronization signal transmitter 2 as the target on which whether or not the pieces of identification information are in agreement with each other should be determined may be mishandled and confused with another one due to environmental deficiency such as wireless radio wave failure (for example, a synchronization signal transmitter 2 having the same ESSID exists).

In view of such a problem, when multiple candidates for the synchronization signal transmitter 2 exist, the determination of whether or not the pieces of identification information are in agreement with each other may also be performed on the other candidate(s). Specifically, the bulb controller 12a of the irradiation apparatus 1 or the panel controller 31 of the imaging apparatus 3 is to perform, for example, the processing illustrated in FIG. 18.

First, the synchronization signal transmitter 2 is searched for (step S71) and determination is made on whether or not any synchronization signal transmitter 2 as a target of connection exists (step S72). Here, if it has been determined that the target exists (Yes in the step S72), then determination is made on whether or not the pieces of identification information are in agreement with each other (step S73). Here, if it has been determined that the pieces of identification information are in agreement with each other (Yes in the step S73), the processes at the time of the agreement (permission of radiation irradiation and the notification of the fact that the pieces of identification information are in agreement with each other in the step S74) are to be performed. Meanwhile, if it has been determined in the step S72 that there is no target (No in the step S72) or if it has been determined in the step S73 that the pieces of identification information are not in agreement with each other (No in the step S73), then determination is made on whether or not there is any other synchronization signal transmitter 2 as a possible target of connection (step S75). Here, if it has been determined that any other target exists, the processing proceeds to the process of the step S73 (the determination of whether or not the pieces of identification information are in agreement with each other). If it has been determined that no other target exists (No in the step S75), then the processes at the time of non-agreement (non-permission of radiation irradiation and notification of the fact of the out-of-synchronization state, the step S76) are to be performed.

By this configuration, the restoration at the time of occurrence of an abnormality can be promptly performed.

Also, the robustness to the environment can be enhanced.

Although embodiments of the present invention have been described and illustrated in detail, the disclosed embodiments are made for purposes of illustration and example only and not limitation. The scope of the present invention should be interpreted by terms of the appended claims.

What is claimed is:

1. A radiation imaging system comprising:
a radiation irradiation apparatus that generates radiation;
a radiation imaging apparatus that generates image data of a radiographic image in accordance with the radiation emitted; and
a synchronization signal transmitter connected to the radiation irradiation apparatus or incorporated in the radiation irradiation apparatus, the synchronization signal transmitter transmitting a synchronization signal to the radiation imaging apparatus, the synchronization signal being used to synchronize operations between the radiation imaging apparatus and the radiation irradiation apparatus, the synchronization signal transmitter storing unique identification information used to identify the synchronization signal transmitter and transmitting the identification information to the radiation irradiation apparatus and the radiation imaging apparatus, respectively, and
the radiation irradiation apparatus or the radiation imaging apparatus including a hardware processor that determines whether or not the identification information received by the radiation irradiation apparatus and the identification information received by the radiation imaging apparatus are in agreement with each other.

2. The radiation imaging system according to claim 1, wherein the identification information is an identifier of the synchronization signal transmitter.

3. The radiation imaging system according to claim 1, wherein the identification information is a combination of an identifier and an access key of a wireless network.

4. The radiation imaging system according to claim 1, wherein the hardware processor restricts irradiation of the radiation by the radiation irradiation apparatus when the hardware processor determines that the identification information received by the radiation irradiation apparatus and the identification information received by the radiation imaging apparatus are not in agreement with each other.

5. The radiation imaging system according to claim 1, wherein the hardware processor uses a communicator and notifies a user about a result of determination of whether or not the identification information received by the radiation irradiation apparatus and the identification information received by the radiation imaging apparatus are in agreement with each other.

6. The radiation imaging system according to claim 1, wherein either of the radiation irradiation apparatus and the radiation imaging apparatus acting as a slave device performs again reception of the identification signal when the hardware processor determines that the identification information received by the radiation irradiation apparatus and the identification information received by the radiation imaging apparatus are not in agreement with each other.

7. A radiation imaging system comprising:
a radiation irradiation apparatus that generates radiation;
a radiation imaging apparatus that generates image data of a radiographic image in accordance with the radiation emitted; and
a synchronization signal transmitter incorporated in the radiation imaging apparatus, the synchronization signal transmitter transmitting a synchronization signal to the radiation irradiation apparatus, the synchronization signal being used to synchronize operations between the radiation irradiation apparatus and the radiation imaging apparatus, the synchronization signal transmitter storing unique identification information used to identify the synchronization signal transmitter and transmitting the identification information to the radiation irradiation apparatus and the radiation imaging apparatus, respectively, and the radiation irradiation apparatus or the radiation imaging apparatus including a hardware processor that determines whether or not the identification information received by the radiation irradiation apparatus and the identification information received by the radiation imaging apparatus are in agreement with each other.

* * * * *